United States Patent
Larkin et al.

(10) Patent No.: US 9,592,255 B2
(45) Date of Patent: Mar. 14, 2017

(54) SCAFFOLD-FREE THREE DIMENSIONAL NERVE FIBROBLAST CONSTRUCTS

(75) Inventors: Lisa M. Larkin, Ann Arbor, MI (US); Ellen M. Arruda, Ann Arbor, MI (US); Jennifer Baltich, Calgary (CA); Aaron Adams, Ypsilanti, MI (US); Leah Hatch-Vallier, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 119 days.

(21) Appl. No.: 13/805,486

(22) PCT Filed: Jul. 1, 2011

(86) PCT No.: PCT/US2011/042830
§ 371 (c)(1),
(2), (4) Date: Mar. 1, 2013

(87) PCT Pub. No.: WO2012/003465
PCT Pub. Date: Jan. 5, 2012

(65) Prior Publication Data
US 2013/0156742 A1 Jun. 20, 2013

Related U.S. Application Data

(60) Provisional application No. 61/360,638, filed on Jul. 1, 2010.

(51) Int. Cl.
*A61K 35/12* (2015.01)
*A61K 35/33* (2015.01)
(Continued)

(52) U.S. Cl.
CPC .............. *A61K 35/33* (2013.01); *A61K 35/30* (2013.01); *A61L 27/383* (2013.01);
(Continued)

(58) Field of Classification Search
None
See application file for complete search history.

(56) References Cited

U.S. PATENT DOCUMENTS 5,190,878 A 3/1993 Wilhelm et al.
5,605,835 A 2/1997 Hu et al.
(Continued)

FOREIGN PATENT DOCUMENTS

WO WO 2009155334 A1 * 12/2009

OTHER PUBLICATIONS

Sanjay Dhar, Eul Sik Yoon, Suraj Kachgal, and Gregory R.D. Evans, Long-Term Maintenance of Neuronally Differentiated Human Adipose Tissue-Derived Stem Cells, 2007, Tissue Engineering, vol. 13, No. 11, pp. 2625-2632.*

(Continued)

*Primary Examiner* — Ralph Gitomer
*Assistant Examiner* — Trent Clarke
(74) *Attorney, Agent, or Firm* — Marshall, Gerstein & Borun LLP

(57) ABSTRACT

The invention relates to scaffold-free three dimensional nerve fibroblast constructs and method of generating the nerve fibroblast constructs. The invention also relates to methods or repairing nerve transection and replacing damaged nerve tissue using the nerve fibroblast constructs of the invention.

5 Claims, 10 Drawing Sheets

A.

B.

C.

D.

(51) Int. Cl.
| | |
|---|---|
| A61K 35/30 | (2015.01) |
| A61L 27/38 | (2006.01) |
| C12N 5/079 | (2010.01) |
| C12N 5/071 | (2010.01) |

(52) U.S. Cl.
CPC ....... *A61L 27/3804* (2013.01); *A61L 27/3878* (2013.01); *A61L 27/3891* (2013.01); *C12N 5/0622* (2013.01); *C12N 5/0697* (2013.01); A61L 2430/32 (2013.01); C12N 2500/32 (2013.01); C12N 2500/38 (2013.01); C12N 2501/11 (2013.01); C12N 2501/115 (2013.01); C12N 2501/15 (2013.01); C12N 2502/08 (2013.01); C12N 2502/086 (2013.01); C12N 2502/1323 (2013.01); C12N 2506/1307 (2013.01); C12N 2506/1384 (2013.01); C12N 2533/10 (2013.01); C12N 2533/52 (2013.01)

(56) References Cited

U.S. PATENT DOCUMENTS

| | | | |
|---|---|---|---|
| 5,688,687 | A | 11/1997 | Palsson et al. |
| 5,888,807 | A | 3/1999 | Palsson et al. |
| 5,985,653 | A | 11/1999 | Armstrong et al. |
| 6,001,642 | A | 12/1999 | Tsao |
| 6,096,653 | A | 8/2000 | Tu et al. |
| 2004/0132184 | A1 | 7/2004 | Dennis et al. |
| 2005/0226856 | A1* | 10/2005 | Ahlfors .................. 424/93.7 |
| 2008/0004713 | A1 | 1/2008 | Nakamura et al. |
| 2008/0193910 | A1 | 8/2008 | Larkin et al. |
| 2008/0199953 | A1* | 8/2008 | Kosnik et al. ............. 435/325 |

OTHER PUBLICATIONS

Robert G. Dennis and Paul E. Kosnik, II, Excitability and Isometric Contractile Properties of Mammalian Skeletal Muscle Constructs Engineered In Vitro, 2000, In Vitro Cellular & Developmental Biology—Animal, vol. 36, No. 5, pp. 327-335.*
Balgude et al., Agarose gel stiffness determines rate of DRG neurite extension in 3D cultures. *Biomaterials*, 22: 1077-84 (2001).
Baltich et al., Development of a scaffoldless three-dimensional engineered nerve using a nerve-fibroblast co-culture. In Vitro *Cell. Dev. Biol. Animal*, 46(5): 438-44 (2010).
Bellamkonda et al., Hydrogel based three-dimensional matrix for neural cells. *J. Biomed. Mater. Res.*, 29: 663-71 (1995).
Bryan et al., Enhanced peripheral nerve regeneration through a poled bioresorbably poly(lactic-co-glycolic acid) guidance channel. *J. Neural Eng.*, 1(2): 91-8 (2004).
Bunge et al., Role of peripheral nerve extracellular matrix in Schwann cell function and in neurite regeneration. *Dev. Neurosci.*, 11: 348-60 (1988).
Calve et al., Engineering of functional tendon. *Tissue Eng.*, 10(5-6): 755-61 (2004).
Ceballos et al., Magnetically aligned collagen gel filling a collagen nerve guide improves peripheral nerve regeneration. *Exp Neurol.*, 258(2): 290-300 (1999).
Chiu, Special article: the development of autologous venous nerve conduit as a clinical entity. In P&S Medical Review, New York: Columbia-Presbyterian Med. Cent. 3(1): (1995).

Deumens et al., Repairing injured peripheral nerves: Bridging the gap. *Prog. Neurobiol.*, 92(3): 245-76 (2010).
Galla et al., Fibrin/Schwann cell matrix in poly-epsilon-caprolactone conduits enhances guided nerve regeneration. *Int. J. Artif. Organs*, 27(2): 127-36 (2004).
Gronthos et al., Surface protein characterization of human adipose tissue-derived stromal cells. *J. Cell. Physiol.*, 189(1): 54-63 (2001).
Huang et al., Biomaterials and strategies for nerve regeneration. *Artif. Organs*, 30(7): 514-22 (2006).
Hudson et al., Engineering strategies for peripheral nerve repair. *The Orthopedic Clinics of North America*, 31(3): 485-98 (2000).
Karagoz et al., Comparison of regeneration results of prefabricated nerve graft, autogenous nerve graft, and vein graft in repair of nerve defects. *Microsurgery*, 29(2): 138-43 (2009).
Locke et al., Concise review: Human adipose-derived stem cells (ASC): Separating promise from clinical need. Stem Cells (Dayton, Ohio) (2011).
Lundborg, Nerve Injury and Repair. New York: Longman Group UK (1988).
Luo et al., A photoliable hydrogel for guided three-dimensional cell growth and migration. *Nat. Mater.*, 3: 249-53 (2004).
Ma et al., Morphological and functional characteristics of three-dimensional engineered bone-ligament-bone constructs following implantation. J. Biomechan. Eng., 131(10): 101017 (2009).
Millesi, Indications and techniques of nerve grafting. In: Gelvertman RH, editor. Operative nerve repair and reconstruction. Philadelphia: Lippincott JB, 525-44 (1991).
Millesi, Briding defects: Autologous nerve grafts. *Acta Neurochir. Suppl.* 100: 37-8 (2007).
Piotrowicz et al,. Nerve guidance channels as drug delivery vehicles. *Biomaterials*. 27(9): 2018-27 (2006).
Radtke et al., Peripheral glial cell differentiation from neurospheres derived from adipose mesenchymal stem cells. Intl. J. Dev. Neurosci.: The Official Journal of the International Society for Developmental Neuroscience, 27(8): 817-23 (2009).
Ray et al.,. Management of nerve gaps: Autografts, allografts, nerve transfers, and end-to-side neurorrhaphy. Exp. Neurol., 223(1): 77-85 (2010).
Rutkowski et al., Synergistic effects of micropatterened biodegradable conduits and Schwann cells on sciatic nerve regeneration. *J. Neural Eng.*, 1: 151-7 (2004).
Schmidt et al., Neural tissue engineering: Strategies for repair and regeneration. *Annu. Rev. Biomed. Eng.* 5: 293-347 (2003).
Seidlits et al., Nanostructured scaffolds for neural applications. *Nanomedicine (Lond.)*, 3(2): 183-99 (2008).
Spilker et al., Contraction of collagen-glycosaminoglycan matrices by peripheral nerve cells in vitro. *Biomaterials*, 22: 1085-93 (2001).
Yamamoto et al., Isolation of multipotent stem cells from mouse adipose tissue. *J. Dermatol. Sci.*, 48(1): 43-52 (2007).
Yu et al., A Laminin and nerve growth factor-laden three-dimensional scaffold for enhanced neurite extension. *Tissue Eng.* 5(4): 291-305 (1999).
Zhu et al., Adipose-derived stem cell: A better stem cell than BMSC. *Cell Biochem. Func.*, 26(6): 664-75 (2008).
International Search Report and Written Opinion of the International Searching Authority, Korean Intellectual Property Office, PCT/US2011/042830, dated Feb. 28, 2012.

* cited by examiner

A.

B.

A.

B.

SCAFFOLD-FREE THREE DIMENSIONAL NERVE FIBROBLAST CONSTRUCTS

This application claims priority to U.S. Provisional Application No. 61/360,638 filed Jul. 1, 2010, which is incorporated herein by reference in its entirety.

This invention was made with government support under AR054778 awarded by the National Institutes of Health. The government has certain rights in the invention.

FIELD OF INVENTION

The invention relates to scaffold-free three dimensional nerve fibroblast constructs and method of generating the nerve fibroblast constructs. The invention also relates to methods or repairing nerve transection and replacing damaged nerve tissue using the nerve fibroblast constructs of the invention.

BACKGROUND

Nerve transection is the most severe neural injury (Schmidt 2003). Following transection, the proximal segments of nerves in the peripheral nervous system are capable of regenerating to restore nerve function (Rutkowski 2004). Myelin debris is removed and neurotrophic factors are released by Schwann cells and macrophages that guide the regenerating axons and allow for restored function (Huang 2006). The current "gold standard" for repairing transected nerves in the peripheral nervous system is an autologous nerve graft (Lundborg 1988, Meek 2008, Schmidt 2003). However, there are several concerns that arise with nerve grafting. Harvesting the donor nerve graft can lead to donor site neuroma, loss of function, and scarring (Taras 2005). Concerns also arise over the limited supply of nerve graft donors (Millesi 1991). The functional recovery from this type of procedure is also has variable, only approaching 80% on average (Hudson 2000, Chiu 1995).

The drawbacks of autologous nerve grafting have led to an increased focus in neural tissue engineering research. Current research focuses on finding an ideal nerve guidance channel for peripheral nerve repair. Nerve guidance channels help direct regenerating axons with nerve-compatible biomaterials and neurotrophic factors (Hudson 2000). They avoid the need for a second surgery as well as the potential risks involved with nerve grafting, including donor site morbidity (Taras 2005). They also provide additional benefits in that they prevent axon escape and can be used in hard to reach locations (Meek 2008). Several requirements must be considered when manufacturing a nerve guidance channel including shape, biocompatibility, wall porosity, degradation rate, mechanical strength, and material electrical conductivity (Huang 2006). The material must be appropriate to allow for the penetration of regenerating axons while not damaging the axons (Balgude 2001). The need for a longitudinal distribution of axons also makes it difficult to design scaffolds for nerve repair (Wang 2009). These requirements place limits on the types of materials that may be used for nerve repair.

Nerve guidance channels are fabricated using synthetic or natural materials, both of which have specific benefits and drawbacks. Synthetic materials are beneficial because they allow for alteration of various properties, including porosity, mechanical strength, and degradation rate (Schmidt 2003, Hudson 2000). Drawbacks to synthetic materials include biocompatibility, immune rejection, poor cell adhesion, and mediocre tissue repair (Schmidt 2003). Natural materials are beneficial because they are more biocompatible and less toxic (Schmidt 2003, Hudson 2000, Taras 2005). Drawbacks, however, include isolation issues (Schmidt 2003). Unfortunately, there are still several complications that may arise with nerve guidance channels regardless of the material used. Most importantly, guidance channels can only currently be used for distances less than 3 cm and nerve grafts must still be used for large gaps (Kemp 2008, Meek 2008).

Current research in tissue engineering has focused on improving nerve guidance channels to enhance nerve regeneration (Hudson 2000, Wang 2009). Current projects have focused on 6 main conduit adaptations: 1) porous channel walls (Huang 2006), 2) neurotrophic factor release (Piotrowicz 2006), 3) incorporation of Schwann cells (Galla 2004), 4) aligned intraluminal matrix (Lu 2005) and 6) electrical properties (Bryan 2004). All of these methods are still faced with the drawbacks of using scaffolds for tissue engineering as mentioned above.

Current experiments aimed at creating three dimensional (3-D) nerve constructs mainly focus on the use of agarose gels and other hydrogel scaffolds (Bellamkonda 1995). Hydrogels are attractive for scaffolds due to their biocompatibility (Luo 2004). The addition of extracellular matrix and neurotrophic factors such as laminin and nerve growth factor to hydrogel scaffolds have led to enhanced neurite extension (Yu 1999). The factor infused hydrogel can be used to fill nerve guidance channels to enhance neurite growth and allow for the development of 3-D nerve repair (Yu 1999). Matrigel™ has also been shown to promote neural growth but is unappealing due to its tumorigenic origins (Bellamkonda 1995). Collagen and collagen-gycosaminoglycan matrices have also proven successful peripheral nerve repair (Spilker 2001). All of these experiments still involve scaffolds and all of the problems that are associated with the use of scaffolds.

Three dimensional fibroblast constructs and muscle constructs from a tissue monolayer can be fabricated (Calve 2004). Unlike fibroblast and muscle cell monolayers, a nerve monolayer does not roll up into a 3-D construct. Muscle monolayers will roll up due to contracting muscle cells and fibroblasts roll up due to tension developed between the cells in the monolayer. A nerve monolayer, however, has no source of strain between cells and will merely continue to branch out in one plane.

Current technologies related to neural tissue engineering focus on using nerve guidance channels for the repair of peripheral nerve injury (Ray 2009, Deumens 2010). These scaffolded guidance channels are often incorporated with combinations of Schwann cells, stem cells, and neurotrophic factors which direct and enhance growth of regenerating nerve (Hudson 2000. While these engineered conduits have found success with small peripheral nerve defects, they are still faced with several drawbacks associated with the use of scaffolds, including biocompatibility, immune rejection, poor cell adhesion, and mediocre tissue repair. The need for a more biocompatible, readily available engineered conduit for repair of larger defects persists. The experiments conducted here present the technology for the development of a scaffoldless three-dimensional engineered neural conduit from a readily available, biocompatible source of cells, adipose-derived stem cells (ASC), which overcomes the drawbacks associated with current autograft and scaffold-based technologies.

Previous work indicated that neural cells would proliferate and form a network of cells across an established monolayer of muscle (Larkin 2006). The objective of the experiments described herein was to use similar technologies to grow a nerve monolayer on an existing fibroblast monolayer so that when the fibroblast monolayer rolls up due to tension between the fibroblast cells, a 3-D construct with an external fibroblast sheath and an internal core of interconnected nerve cells would form. To accomplish this, nerve cells suspended in neural basal medium (NBM) were seeded on a confluent monolayer of fibroblasts. Once the neural cells had proliferated and migrated across the fibroblast monolayer, the media is changed to stimulate the fibroblast monolayer to roll up into a 3-D construct effectively forming a 3-D fibroblast-nerve construct as a result. These 3-D fibroblast nerve constructs may be used for surgical repair of nerve transection.

SUMMARY OF INVENTION

The invention provides for methods of generating a scaffold-free, three-dimensional nerve fibroblast construct comprising the step of: growing nerve cells on a static and confluent monolayer of fibroblasts without an exogenous scaffold and under conditions that induce the monolayer of fibroblasts to contract to generate a co-culture of fibroblast and nerve cells, wherein the fibroblasts that are induced to contract, surround the nerve cells generating a three-dimensional nerve fibroblast construct. In contracting, the fibroblast cells roll up around the nerve cells. In one aspect, the conditions that induce the monolayer of fibroblasts to contract comprise growing the nerve cells and fibroblasts in media comprising ascorbic acid and transforming growth factor-beta (TGF-β).

The methods of generating scaffold-free, three-dimensional nerve fibroblast constructs may be carried out with fibroblasts derived from adipose-derived stem cells or nerve cells derived from adipose-derived stem cells. Furthermore, the methods of the invention may be carried out with fibroblasts and nerves cells that are both derived from adipose-derived stem cells.

A "static monolayer" refers to a layer of living cells that are in a non-proliferating state.

A "confluent monolayer" refers to a continuous layer of cells in culture wherein the cells are touching but do not grow atop each other or forms clumps of cells. Confluent cell cultures may be defined by percent confluence which refers to the percentage of the culture dish that is covered with the monolayer of cells, such as 70% confluent cell culture, 75% confluent cell culture, 80% confluent cell culture, 85% confluent cell culture, 95% confluent cell culture, 98% confluent cell culture or 99% confluent cell culture. 100% confluent cell culture refers to when an entire culture dish is covered with a monolayer of cells.

In one embodiment, the methods of the invention are carried out wherein the fibroblasts and nerve cells are grown on a substrate. The term "substrate" refers to a surface or medium on which the cells and constructs of the invention grow or attach. In one aspect of the invention, the substrate is a culture plate coated with a silicon elastomer and laminin. Exemplary silicon elastomers include polydimethyl siloxane (PDSM) such as SYLGARD. In another aspect of the invention, the substrate is a natural or synthetic extracellular matrix such as matrigel, collagen, laminin, fibronectin, elastin and fibrin The invention also provides a scaffold-free, three-dimensional nerve fibroblast construct generated by any of the method of the invention.

The invention also provides a self-organizing, scaffold-free, three-dimensional nerve fibroblast construct comprising nerve cells surrounded by an external monolayer of fibroblasts. The fibroblasts and/or nerve cells within the self-organizing, scaffold-free, three-dimensional nerve fibroblast construct may be derived from adipose-derived stem cells.

In a further embodiment, the invention provides a three-dimensional co-culture comprising nerve cells and an external monolayer of fibroblasts, wherein the fibroblasts are contracted around and surround the nerve cells. The fibroblasts and/or nerve cells within the three-dimensional co-cultures nerve fibroblast construct may be derived from adipose-derived stem cells. The invention also provides methods of repairing a nerve transection in a subject comprising inserting the three-dimensional nerve fibroblast construct of the invention in a subject in need to repair the nerve transection. These methods, in one aspect, are carried out wherein the nerve fibroblast construct is inserted surgically.

In another embodiment, the invention provides for a method of replacing damaged nerve tissue in a subject comprising inserting the three-dimensional nerve fibroblast construct of the invention in a subject in need to replace the damaged nerve tissue. These methods, in one aspect are carried out wherein the nerve fibroblast construct is inserted surgically.

In a further embodiment, the invention provides for a self-organizing, scaffold-free, three-dimensional nerve fibroblast construct comprising nerve cells surrounded by an external monolayer of fibroblasts for use in repairing a nerve transaction. The invention also provides for a self-organizing, scaffold-free, three-dimensional nerve fibroblast construct comprising nerve cells surrounded by an external monolayer of fibroblasts for use in replacing damaged nerve tissue. The fibroblasts and/or nerve cells within these constructs may be derived from adipiose-derived stem cells.

The invention also provides for the use of a self-organizing, scaffold-free, three-dimensional nerve fibroblast construct comprising nerve cells surrounded by an external monolayer of fibroblasts for preparation of a medicament for repairing damaged nerve tissue. In addition, the invention provides for the use of a self-organizing, scaffold-free, three-dimensional nerve fibroblast construct comprising nerve cells surrounded by an external monolayer of fibroblasts for the preparation of a medicament for replacing damaged nerve tissue. The fibroblasts and/or nerve cells within these constructs may be derived from adipose-derived stem cells. The invention also provides systems for forming a three-dimensional nerve fibroblast construct comprising: a confluent monolayer of fibroblasts provided on a substrate without an exogenous scaffold, the fibroblasts existing in a static state; and nerve cells on the monolayer of fibroblasts, the nerve cells grown under conditions that induce the monolayer of fibroblasts to contract and surround the nerve cells. The fibroblasts and/or nerve cells within the systems of the invention may be derived from adipiose-derived stem cells.

DETAILED DESCRIPTION

Figure 1:
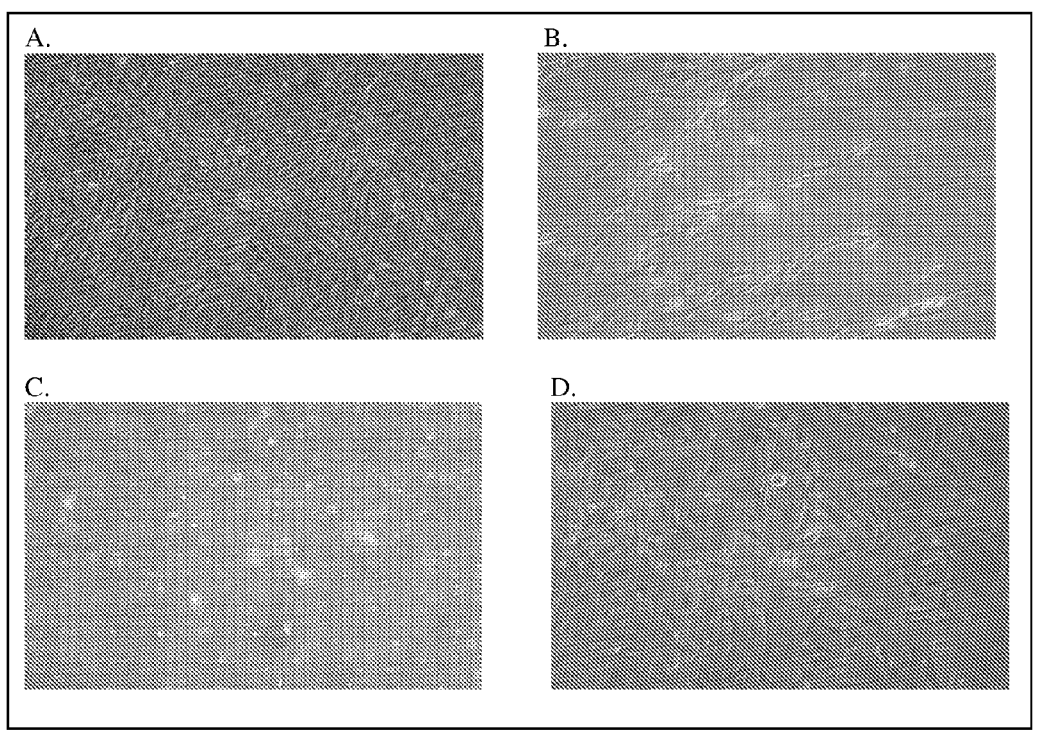
FIG. 1 demonstrates the effect of media on the formation of a confluent monolayer of fibroblast. Fibroblasts were seeded at a density of $1 \times 10^5$ cells per plate and viewed 7 days after proliferation on a laminin coated sylgard plate. The cells were cultured for 5 days with either Growth Media (GMA) (A), 50% GMA/%50 Neural Basal Medium (NBM) (B) NBM, and NBM and then switched to GMA. Images were viewed at 50×.
Figure 2:
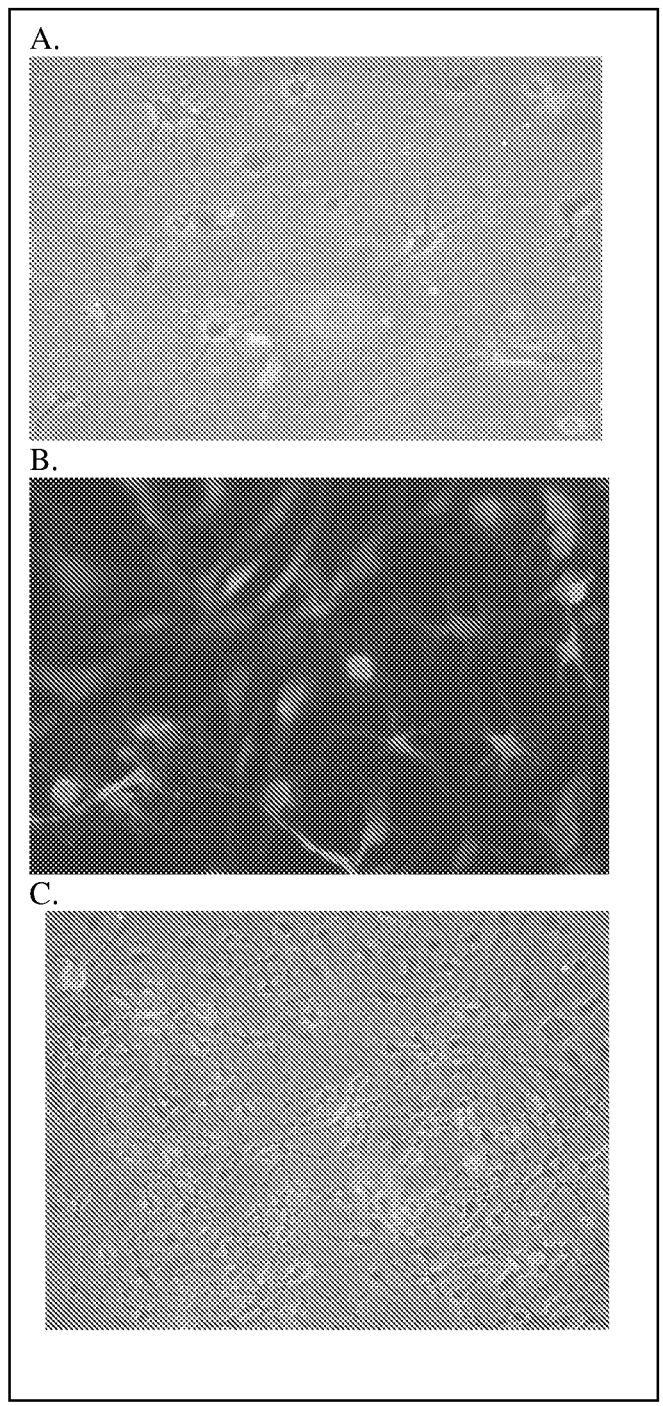
FIG. 2 demonstrates the effect of co-culturing E-15 neural cells on an established monolayer of fibroblasts: A) Neural cells on fibroblast monolayer after 3 days on NBM, B) Neural cells on fibroblast monolayer stained with S100 and DAPI, C) Neural cells on fibroblast monolayer after 7 days on NBM formed a confluent network. Note the decreased presence of fibroblasts. Images A and B was viewed at 100×. Image C was viewed at 50×.
Figure 3:
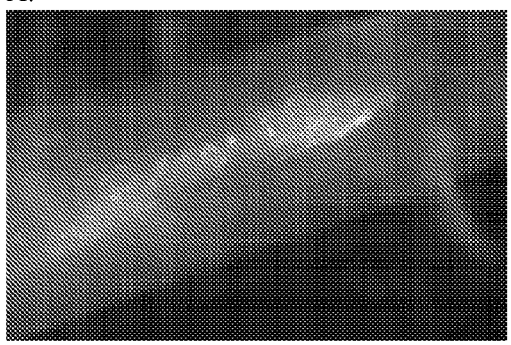
FIG. 3 provides immunohistological characterization of a 3-D nerve-fibroblast construct stained with A) S100 and DAPI, B) S100, DAPI, and Collagen 1 and C & D) β3-tubulin and DAPI. Images viewed at 50×.
Figure 3:
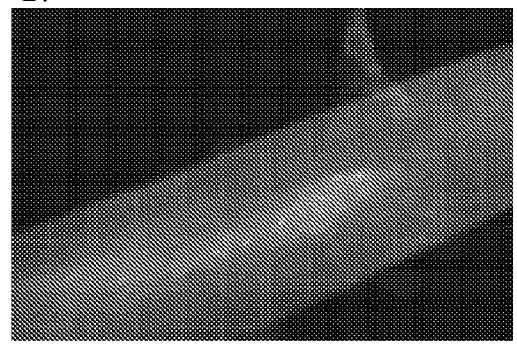
Figure 3:
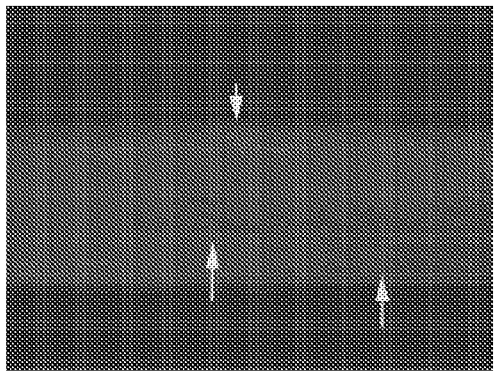
Figure 3:
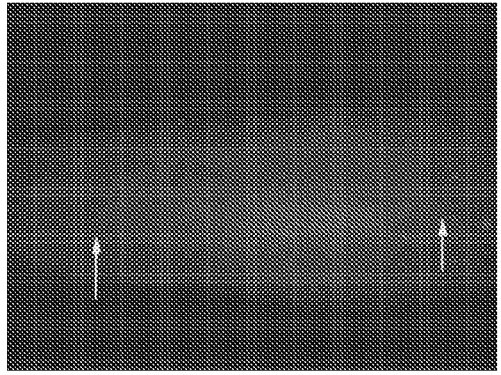

The present invention provides method of engineering three-dimensional, self-organizing, nerve fibroblast constructs from fibroblasts and nerve cells without the use of an exogenous scaffold. After approximately 3 days the fibroblast monolayer became 80-90% confluent and nerve cells suspended in serum-free NBM were added to the plates. After approximately 10 days of co-culture in NBM, the nerve cells reach 70-80% confluence across the fibroblast monolayer. At this point, the medium was switched to DMA containing ascorbic acid and TGF-β. After approximately 4 days on DMA, the monolayer rolls up around the constraint pins and forms a 3-D configuration. Immunohistochemistry analysis demonstrates an inner core of nerve cells surrounded by an external layer of fibroblasts.

The present invention also provides for three-dimensional, self-organizing, nerve fibroblast constructs that comprise fibroblast and nerve cells which were derived from adipose-derived stem cells (ASCs) that were permanently induced to a fibroblast lineage and neural lineages. The studies described herein demonstrate the differentiation of ASCs to fibroblastic and neural lineages, establishment of a co-culture of both cell types, and co-culture fabrication into a three-dimensional scaffold-less engineered neural conduit (also referred to herein as nerve fibroblast constructs). Immunohistochemisty was used to confirm ASC differentiation and demonstrated ASC-derived fibroblasts forming an epineueral-like sheath surrounding an inner neural network of glial like cells.

Immunohistochemistry indicates that a nerve fibroblast construct with a fibroblast exterior was successfully engineered. Such constructs avoid the complications found with scaffolds such as immune rejection and degradation rate issues, as well as those associated with grafting such as availability and donor site morbidity. They are also unique in that they have a fibroblast sheath consisting of Collagen I similar to that found in native peripheral nerve tissue (Bunge et al. 1989). This scaffoldless 3-D nerve-fibroblast construct of the invention show potential for replacement of damaged nerve tissue. The ability of the engineered scaffoldless 3-D) nerve construct to conduct an electrical signal may make it advantageous for nerve repair. The conductive property of the construct may enhance the restoration of the electrical pathways to the target tissue. One might assume that the conduction velocity of the construct will improve following in vivo implantation in a nerve repair model.

As required, detailed embodiments of the present invention are disclosed herein; however, it is to be understood that the disclosed embodiments are merely exemplary of the invention that may be embodied in various and alternative forms. Therefore, specific structural and functional details disclosed herein are not to be interpreted as limiting, but merely as a representative basis for teaching one skilled in the art to variously employ the present invention.

By way of example, the fibroblast-nerve constructs and systems and methods for their production according to the present invention are described with reference to the use of tissue harvested from rats. However, it is fully contemplated that tissue from any mammal, including human beings, could be similarly utilized according to the method described herein. The constructs, systems and methods of the present invention are not intended to be limited to one particular cell origin or age, construct shape or dimensions, time frame, component concentration, or culture condition. One skilled in the art can readily appreciate that various modifications can be made to the constructs, systems and methods described herein without departing from the scope of the invention disclosed.

For example, primary human dermal fibroblasts (such as those available from Invitrogen (Carlsbad, Calif.), Lifeline Cell Technology (Oceanside, Calif.) and Lonza (Walkersville, Md.)), lung fibroblasts, aortic fibroblasts and periodontal ligament fibroblasts (such as those available from Lonza (Walkersville, Md.)) may be used to generate the fibroblast-nerve constructs of the invention. In addition, the following exemplary fibroblast cell lines (available from the ATCC (Manassas, Va.)) may be used to generate the fibroblast-nerve constructs of the invention: Detroit 551 (CCL-110), Detroit 548 (CCL-116), Detroit 573 (CCL-117), HG-261 (CCL-122), C 211 (CCL-123 and Amdur II (CCL-124).

Adipose-derived stem cells (ASC) may also be permanently induced to a fibroblast lineage and neural lineages and co-cultures of these cells may be used to fabricate and characterize an engineered fibroblast-nerve construct. The invention combines the approach of utilizing stem cells in nerve repair technologies with the technique for fabricating scaffold-less neural conduits as described by Radtke 2009, Baltich 2010. The studies described herein demonstrate the differentiation of ASCs to fibroblastic and neural lineages, establishment of a co-culture of both cell types, and co-culture fabrication into a three-dimensional scaffold-less engineered neural conduit (also referred to herein as nerve fibroblast constructs).

The utilization of ASC addresses and eliminates the most limiting factor in successful repair of peripheral nerve injuries, availability of autologous nerve tissue. The ASCs used in the fabrication of the Nerve Fibroblast construct are abundant and biocompatible and thus eliminate the concerns of availability and immune rejection which are observed with most engineered conduits. Immunohistochemical analysis of the ASC derived a Nerve Fibroblast construct described in Example 7 indicates that a 3-D nerve construct with a fibroblast exterior and interior neural network was successfully engineered. Thus, this scaffoldless three-dimensional ASC-derived nerve-fibroblast conduit is contemplated as a replacement of damaged nerve tissue.

Unless otherwise indicated, all solutions and media described herein may be prepared and stored at 4° C. before, and then warmed to 37° C. in a heated water bath immediately before use. It is understood that all reagent measurements, materials, submersion times, and other values described herein are approximate, and can be reasonably varied without affecting the method and resulting constructs. Furthermore, the approximate volumes of reagents within solutions described herein may be altered to provide a solution with reagents having similar volume ratios.

According to a first aspect of the present invention, a construct, system and method are provided for producing self-organized, three-dimensional nerve fibroblast constructs solely from fibroblasts and nerve cells, without the use of artificial, exogenous scaffolding. The systems, constructs and methods described herein bypass the many design challenges and limitations associated with the engineering of nerve constructs with exogenous scaffolding. Detection of β-tubulin indicates the presence of nerve cells. DAPI will detect the nucleus.

The systems, constructs, and methods of engineering nerve fibroblast structures according to the present invention, in which cells are cultured to assemble their own three dimensional scaffolding, bypass the complexity of engineering a scaffold and shifts the paradigm of nerve tissue engineering to the guided self-assembly of an autogenous extracellular matrix. Furthermore, the system and method described herein utilize the culture of nerve cells and fibroblasts that can be isolated from autologous sources without major ethical issues, and may be used clinically with minimal risk of rejection.

An additional goal of tissue engineering is to fabricate tissue for use in repair of tissue damaged as a result of disease, trauma and surgery, especially for cases where the amount of nerve loss creates a critical defect which will not repair by normal self-repair processes and needs intervention. In further accordance with the present invention, utilization of the nerve fibroblast construct to repair a critical nerve defect, transections and injuries may produce a new nerve segment in which the engineered construct will incorporate into the host and form a viable interface that will restore the functionality.

Tissue Culture Vessels

Those of ordinary skill in the art will readily appreciate that the cell culture and bioengineering methodologies described herein may be carried out in on a variety of environments or substrates (i.e., vessels or containers). Fibroblast cells are anchorage dependent, and therefore to grow in culture these cells require a nontoxic, biologically inert, and optically transparent surface that will allow cells to attach and allow movement for growth. Tissue culture vessels or plates include specially-treated polystyrene plastic that are supplied sterile and are disposable. These include Petri dishes, multi-well plates, microtiter plates, roller bottles, screwcap flasks (T-25, T-75, T-150 $cm^2$ of surface area), culture bags or any container capable of holding cells, preferably in a sterile environment.

In one embodiment of the present invention, a bioreactor is also useful for bioengineering the nerve fibroblast constructs. For example, several manufacturers currently make devices that can be used to grow cells and be used in combination with the methods of the present invention. See for example, Celdyne Corp., Houston, Tex.; Unisyn Technologies, Hopkinton, Mass.; Synthecon, Inc. Houston, Tex.; Aastrom Biosciences, Inc. Ann Arbor, Mich.; Wave Biotech LLC, Bedminster, N.J. Further, patents covering such bioreactors include U.S. Pat. Nos. 6,096,532; 6,001,642, 5,985, 653; 5,888,807; 5,688,687, 5,605,835, 5,190,878, which are incorporated herein by reference.

There are a number of different kinds of bioreactors, devices designed to provide a low-shear, high nutrient perfusion environment, available on the market. For example, the invention may be carried out in a rotating wall bioreactor, which consists of a small inner cylinder, the substrate for the electrospinning process, positioned inside a larger outer cylinder. Although the electrospun matrix can be fabricated on the inner cylinder, other locations within the bioreactor also may be used for placement of the matrix for seeding. The gap between the inner and outer cylinders serves as the culture vessel space for cells. Culture medium is oxygenated via an external hydrophobic membrane. The low shear environment of the rotating bioreactor promotes cell-cell and cell-extracellular matrix (ECM) interactions without the damage or "washing away" of nutrients that occurs with active stirring.

Matrix Materials

To generate the nerve fibroblast constructs, the fibroblasts are grown in a cell culture vessel containing one or more extracellular matrix proteins. In one embodiment, fibroblasts cells are grown on a culture vessel coated with laminin.

The type of matrix that may coat the substrate is virtually limitless and may include both biological and synthetic matrices. The matrix will have all the features commonly associated with being "biocompatible," in that it is in a form that does not produce an adverse, allergic or other untoward reaction when administered to a mammalian host. Such matrices may be formed from either natural or synthetic materials.

It is contemplated that the nerve fibroblast construct may serve as a replacement organ and may be inserted in vivo to treat mammals exhibiting nerve transaction or damage. For insertion of the nerve fibroblast construct into a mammal in need, the matrices may be fabricated from biodegradable materials that will erode over time in the body to yield a completely natural tissue. These matrices will not induce any chronic inflammatory responses, and cannot serve as a long-term site for infection. Biodegradable polymers have been utilized to engineer tissues that will be structurally integrated with the host tissue. In addition, the use of synthetic, biodegradable matrices will often be advantageous as the degradation time of such synthetic matrices can be designed to coincide with the formation of a new tissue from the cultured cells.

It will of course be understood that biodegradable matrices for use in the invention are not confined to being synthetic matrices. A number of naturally-derived matrix-like materials may be used that will eventually biodegrade in an in vivo environment. Thus, in the context of the present invention, the term biodegradable is not necessarily synonymous with synthetic matrices.

The choice of matrix material will differ according to the particular circumstances and the type of fibroblast cell used. Physical and chemical characteristics, such as, e.g., biocompatibility, biodegradability, strength, rigidity, interface properties and even cosmetic appearance, may be considered in choosing a matrix, as is well known to those of skill in the art. Appropriate matrices will act as in situ scaffolding through which mammalian repair cells may migrate.

Possible non-biodegradable matrices include non-biodegradable polymers such as semipermeable polymers such as poly(acrylonitrile-co-vinyl chloride), polylysine, cellulose acetate and polysulfone. Although generally intended for use in immobilized cells, the use of such polymers in the context of the present invention is certainly not excluded. These polymers may also be used with a variety of gels, including alginate and polyphosphazenes.

Polyphosphazenes are synthetic polymers, and aqueous solutions of polyphosphazenes will gel in the presence of specific ions. These polymers can be used in the same manner as alginate. The exceedingly stable backbone of these synthetic polymers allows significant alterations in side-group functionality without losing the gentle, physiologic gelling conditions.

There are advantages and disadvantages of both natural materials, e.g., collagens, and synthetic materials, e.g., polyglycolic acids. Synthetic materials that incorporate design concepts or specific biological activities of natural biomaterials may combine the advantages of both types of materials. The reproducible, large-scale synthesis and flexible properties of synthetic polymers can be combined with the biocompatibility and biological activity of natural materials. Such materials may be used in this invention.

Amino acid sequences in ECM molecules that are responsible for specific biological activities, e.g., cell binding, have been identified in recent years. This information allows researchers to design synthetic materials that are capable of precise cellular interactions. Genetic engineering approaches are being utilized to prepare artificial proteins with a desired backbone structure and amino acid side chains that promote cell adhesion. These artificial proteins can be expressed in bacterial cells, isolated and purified, and utilized to form matrices or coat other surfaces. This approach offers tremendous control over both the properties (bulk and surface) of the material, and its ability to interact with cells.

Traditional synthetic routes are also being used to develop biodegradable polymers that contain cell recognition peptides as side chains. The advantages of synthetic polymers, such as polylactide, can be combined with the specific biological activity of ECM molecules with this approach. A similar approach is the synthesis of short amino acid chains containing a desired functional group that can be covalently bonded or adsorbed onto matrices fabricated from other synthetic materials. Such biomimetic synthetic polymers and cell-adhesion peptides are proposed for use as implants for tissue regeneration and transplantation. These and any of the foregoing or other "second generation" matrices may be used in the context of the present invention.

Methods of Repairing Damaged Nerves

The invention provides for methods of repairing nerve transections and replacing damaged nerves using the nerve fibroblast constructs of the invention. Nerve injuries, including transactions are caused by physical trauma such as, contusion, stretch, laceration, or local anesthetic toxicity. Nerve injuries are commonly caused by blunt trauma or from penetrating missiles, such as bullets, or other objects. In addition, nerve injury may be associated with fractures, such a humeral fractures, and fracture-dislocations such as shoulder dislocations. Extreme cold temperatures also cause nerve injuries. Furthermore, nerves can be injured during the physiological healing process, such as compression of the sciatic nerve by scar formation and massive heterotopic ossification after hip trauma. Nerve injury can also be caused by diabetes, cancers, autoimmune disease such as multiple sclerosis, Guillain-Barre Syndrome, myasthenia gravis, lupus and inflammatory bowel disease, and infectious diseases such as Lyme disease, Hepatitis C, HIV and the Herpes virus. Exemplary nerve injuries include compression, stretching or laceration of the radial nerve, median nerve, ulnar nerve and sciatic nerve.

EXAMPLES

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

Example 1 described a method of preparing a self-organized fibroblast monolayer. Example 2 describes the isolation of nerve cells. Example 3 describes the formation of a three-dimensional nerve fibroblast construct. Example 4 describes measurement of nerve conduction velocities of a three-dimensional nerve fibroblast construct. Example 5 describes functional evaluation of a three-dimensional nerve fibroblast construct. Example 6 describes the analysis of the nerve fibroblast construct in periphereal nerve injury repair. Example 7 describes utilization of ASC to fabricate scaffoldless three-dimensional nerve fibroblast constructs.

Example 1

Preparation of Self Organized Fibroblast Monolayer

Pregnant Fischer 344 rats (Charles River Laboratories, Wilmington, Mass.) and embryonic day 15 (E15) prenatal rats were used to obtain connective tissue. All animals were acclimated to the light cycle and temperature conditions of the colony for one week before surgery. At day E15, Achilles tendons were removed from the pregnant rats and E15 fetuses were cesarean delivered and fetal spinal cords were obtained. The animals were killed with an overdose of pentobarbital. All animal care and animal surgery were in accordance with the Guide for Care and Use of Laboratory Animals (Public Health Service, 19965, NIH Publication No. 85-23).

All media were stored at 4° C. until use and warmed to 37° C. in a heated water bath for 20 minutes before use. Growth medium with antibiotic-antimycotic mixture (ABAM) (denoted herein as "GMA") consisted of 400 ml HAM F-12 nutrient mixture (Gibco BRL), 100 ml fetal bovine serum (FBS) (Gibco BRL), and 5 ml ABAM. Differentiation medium with ABAM (denoted herein as "DMA") consisted of 465 ml Dulbecco's modified Eagle medium (DMEM) (Gibco BRL), 35 ml 100% horse serum albumin (Gibco BRL), and 5 ml ABAM. Neural basal medium (denoted herein as "NBM") consisted of 500 ml neural basal medium with 5 ml $N_2$ supplement.

Each 35-mm plate was coated with 1.5 ml of SYLGARD (Dow Chemical Corporation, Midland, Mich.; type 184 silicon elastomer) and cured for 3 weeks before use. The plates were then sprayed with 70% ethanol and washed with 3 ml Dulbecco's phosphate buffered saline (DPBS). The DPBS was aspirated off and then the plates were coated with a solution of 3 ml DPBS with 20 mg of laminin. The plates were left to dry overnight in the hood then rinsed again with 2 ml DPBS for five minutes. Each plate was then covered with 1 ml GMA and decontaminated with UV light for one hour. The plates were stored in 37° C., 5% carbon dioxide incubator for one day before plating the tendon cells.

Achilles tendons were surgically removed from Fischer 344 retired breeder rats (Charles River Laboratories). Tendon fibroblasts were isolated from the Achilles tendon by dissociating the tendons in 1 mg/ml type II collagenase (Worthington Biochemical, Lakewood, N.J.) in DMEM plus 2% ABAM. The cells were placed in the 37° C. incubator overnight to break down the extra cellular matrix. The cell solution was then centrifuged at 100 g for 5 minutes and the supernatant was aspirated off just above the cell pellet. The cells were resuspended in 8 ml of GMA and plated on 100-mm-diameter tissue culture dishes. The media on the plate was changed very 48 hours and at 90% confluence the cells were passaged on to two new 100-mm plates.

After two to three passages the cells were treated with 1 ml of 0.25% trypsin and placed on the cell shaker for 20 minutes. The cells were then plated at a density of $2.0 \times 10^5$ cells per plate with GMA and 150 ml of L-ascorbic acid 2 phosphate (Sigma-Aldrich, St Louis, Mo.) on to the 35-mm laminin coated plates. Fresh media consisting of 1.5 ml GMA with 30 μl Ascorbic Acid and 10 μl TGF-β TGF-β was added to each plate every 48 hours. When the plates were at 90% confluence, media was removed and replaced with 1.5 ml of nerve cells (isolated as described below) suspended in NBM ($1.0 \times 10^5$ cells) were added to the plates.

Example 2

Isolation of Nerve Cells

Spinal cords from E-15 fetal rats were surgically removed as described in Example 1, and placed in a 100-mm dish with HAM F-12 nutrient mixture (Gibco BRL). The spinal cords were collectively rinsed with fresh Ham F-12 and placed in a new 100-mm dish with 8 ml Ham F-12 nutrient mixture (Gibco BRL). The spinal cords were then cut into small pieces, approximated 1-2 mm, and placed in a 50 ml conical with 1 ml 0.25% trypsin and 10 ml Ham F-12 nutrient mixture (Gibco BRL) and placed in the 37° C. hot water bath for 20 minutes. A 100 mm cell strainer was used to strain the spinal cord mixture and the strained spinal cord pieces were discarded. An additional 0.5 ml bovine serum albumin (BSA) 4% weight volume was added to the nerve cell suspension and the solution was then centrifuged at 1500 RPM for 10 minutes. The supernatant was aspirated off just above the cell pellet and 5 ml NBM was added to the conical. The cell suspension was mixed thoroughly, cell density determined and the volume of NBM was adjusted to achieve a final plating density of $1.0 \times 10^5$ cells per 1.5 ml. Neural cells were then seeded on to the 35-mm plates containing the fibroblast monolayer, replacing the GMA media currently on the fibroblast plates. The plates were stored in the 37° C. incubator and NBM media was changed every 48 hours.

Example 3

Formation of Three-Dimensional Nerve-Fibroblast Construct

Once the nerve cells had proliferated and migrated to create network that covered approximately 70-80% of the plate (approximately 10 days), the medium was switched from NBM to 1.5 ml DMA with 30 μl TGF-β and 15 μl L-ascorbic acid 2 phosphate. Each plate was pinned with two sets of constraint pins at 12 mm and 14 mm apart. The medium was replaced every 48 hours. The plates would usually roll up after approximately 4-5 days on DMA. After approximately 4 days on DMA, the monolayer rolls up around the constraint pins and forms a 3-D configuration.

Immunohistochemistry shows an inner core of nerve cells surrounded by an external layer of fibroblasts. Immunofluorescent staining was performed to detect the presence of Collagen I, S100, β3-tubulin, and double-stranded DNA. The fibroblast-nerve monolayer was rinsed three times for 10 min each with DPBS then incubated 4% paraformaldehyde (Electron Microscopy Sciences, Hatfield, Pa.) for 1 hour. Each plate was rinsed twice with DPBS for 10 minutes then incubated with 0.5% Triton X100 (Sigma, St. Louis, Mo.) for 10 minutes. The plates were then rinsed two times for 10 minutes each with DPBS and then blocked with DPBS containing 5% donkey serum (DS; Jackson ImmunoResearch Labs, Inc, West Grove, Pa.) for 30 minutes. The plates were then incubated for 2 hours in collagen I (from goat host; 1:200) and S100 or β3-tubulin (from rabbit host; 1:200) in DPBS containing 1% DS. After three additional rinses with DPBS, the plates were incubated with both Cy-3-conjugated AffiniPure donkey anti-goat IgG and fluorescein isothiocyanate-conjugated AffiniPure donkey anti-rabbit IgG (1:500 dilution; Jackson ImmunoResearch Labs, Inc, West Grove, Pa.) for 1 hour. Each plate was then incubated with DAPI (1:500 dilution; Sigma, St. Louis, Mo.) for 10 minutes then rinsed a final time with DPBS. A Leica DMIRB inverted microscope fitted with an Olympus DP-30 high sensitivity grayscale CCD camera was used to image the constructs. Images were viewed at either ×50 or ×100. The external layer of fibroblast stained with collagen I and the inner core of nerve cells stained with S100 (astrocyte derived growth factor) or β3-tubulin. Neural markers were absent from the fibroblast only construct. Therefore, the immunohistological analysis demonstrates a collagen sheath surrounding neural cell bodies running along the interior.

The timeline and methodology chosen resulted from several experiments which studied the influence of various medium and co-culturing techniques on the proliferation of nerve and fibroblast cells in co-culture. Experiments were conducted to test the viability of fibroblasts and nerve cells in NBM, GMA, and 50/50 mixtures of NBM and GMA.

Experiments were also conducted to investigate the affect of the timing on the seeding of the nerve cells with the fibroblasts. Thus, the two cell types were seeded simultaneously versus allowing the fibroblasts to become confluent before the addition of nerve cells. It was found that when fibroblasts and nerve cells were plated simultaneously, the fibroblasts would dominate the plate and the nerve cells were out competed for space on the plate and did not have a chance to proliferate. These experiments suggested that the fibroblasts need to form a monolayer before the nerve cells are added to the plates in order to generate a fibroblast exterior and neural interior.

In addition, these experiments demonstrated that fibroblasts appear to become dormant when cultured in NBM, neither proliferating nor dying. The fibroblasts grow slower in a mixture of 50/50 mixture of GMA and NBM compared to GMA alone (FIG. 1). Once the media was changed back to GMA, the fibroblasts immediately began to proliferating again (FIG. 1D). The changes in fibroblast growth rate occurred due to the lack of serum in the NBM, because the addition of serum to NBM allowed the fibroblast to proliferate and form a confluent monolayer. These experiments suggested that a fibroblast monolayer may be able to survive and be held in a static state in NBM, which inhibited contraction of the fibroblasts and allowed the nerve cells to grow. The medium studies also demonstrated that the nerve cells did not grow as well in GMA or in a 50/50 mixture of GMA and NBM as opposed to NBM alone.

These studies demonstrate that a multiple step process initially generating a monolayer of fibroblasts on GMA prior to the addition of NBM, and then seeding the nerve cells onto the fibroblast monolayer suspended in NBM to create a co-culture in which the nerve cells form a network on top of the fibroblast monolayer before switching to DMA is an effective method developing a three-dimensional nerve fibroblast construct. Once the co-culture is formed, the media is changed to DMA to promote the fibroblasts growth once again. With the growth of fibroblasts, the monolayer rolls up (contract) around the constraint pins effectively forming a core of nerve cells surrounded by an exterior of fibroblasts.

Example 4

Measurement of Nerve Conduction Velocities of Nerve Fibroblast Construct

Sciatic nerve conduction velocities of neonatal rats ranging from 1 to 4 weeks of age were measured following the method of Karagoz et al. (*Microsurgery*, 29(2): 138-143, 2009). Briefly, the sciatic nerve was isolated and exposed. The stimulator of a Viasys TECA Synergy N2 EMG machine was placed proximal to the sciatic nerve. The recording and reference wires were placed in the gastrocnemius muscle. The nerve was stimulated with EMG settings of 0.3 mA and conduction velocities were measured for both the nerve-only construct and the control (fibroblast-only) construct within 1 week of construct formation. Medium was replaced with DPBS (Gibco BRL) to limit background signal. The stimulator was placed under one end of the construct and the recording and reference wires under the other. A ground wire was placed in the dish. Approximately 20 mm away from the construct, nerve conduction velocities were measured in triplicate at 23° C.

The nerve conduction velocities increased with age in the neonatal sciatic nerve, ranging from 2.21±0.12 m/s at 1 week to 15.30±0.27 m/s at 4 weeks. The nerve conduction of the engineered nerve fibroblast construct was equivalent to that observed in the sciatic nerve of the 4-week-old neonatal rat and approximately 50% of that observed in the 12-week-old adult sciatic nerve, 12.50±0.13 and 21.24±0.77 m/s, respectively. In contrast, the fibroblast-only construct reached a velocity of 2.38±0.16 m/s, comparable to a 1 week neonatal sciatic nerve.

Example 5

Functional Evaluation of Nerve Fibroblast Constructs

Following traumatic injury to the peripheral nervous system, nerves are capable of self-regeneration and restoration of function if the injured area is less than 2 cm, termed non-critical. Critical gaps however require surgical intervention.

Two models of nerve repair experiments were used to functionally evaluate the nerve fibroblast constructs of the invention. These models were used to (i) investigate significant immune rejection or scar formation at the repair site, resulting from the construct, (ii) observe and quantify any nerve regeneration through the nerve fibroblast construct, (iii) measure nerve conduction velocity through the nerve fibroblast to demonstrate restorative function, and (iv) investigate whether the nerve fibroblast construct, after a period of nerve regeneration, reached the target muscle and elicited force production in targeted tissues and thereby maintained muscle mass.

Non-Critical Nerve Gap Model

The first nerve repair model was a non-critical gap experiment in which a gap (of 1 cm) in the tibial nerve was repaired using either the engineered nerve fibroblast construct or a control construct which comprised fibroblasts alone. After 28 days of recovery, the nerve conduction velocity, maintenance of gastrocnemius muscle mass, and force production was evaluated for the nerve fibroblast constructs and the control construct.

After the 28 day recovery period, the constructs were sectioned midway between the proximal and distal ends. The non-transected peroneal nerve adjacent to the constructs was also sectioned as a histological control. Nerve regeneration, exhibited by the presence of neuronal adhesion molecule NCAM, was observed for both the nerve fibroblast construct and the control construct. Regenerating nerve filled approximately 26% of the engineered control construct, and nerve regeneration was more complete, filling approximately 100% of the nerve fibroblast construct.

The functional evaluation of the non-critical nerve model 28 days following repair showed significant restoration of nerve conduction velocity. While the histology of the fibroblast construct showed limited nerve regeneration, it elicited a nerve conduction velocity comparable to the engineered nerve fibroblast construct. Both repairs resulted in approximately 75% of non-denervated tibial nerve conduction velocity.

Figure 4:
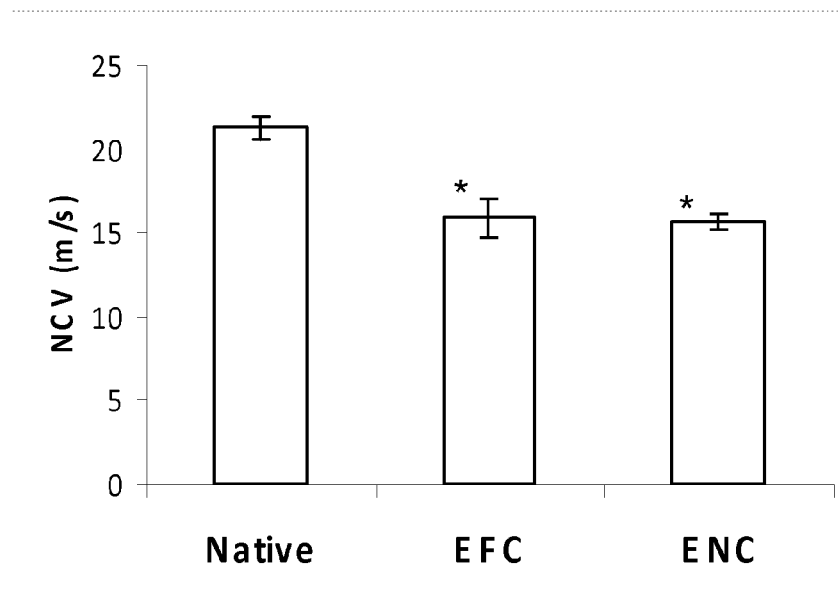
FIG. 4 provides the nerve conduction velocity and the gastrocnemius muscle mass to body ratio in the non-critical nerve gap model. In the top panel, the nerve conduction velocity for the fibroblast construct (EFC; control) and the nerve fibroblast construct (ENC) are statistically significant from native nerve: *p≤0.05; native, n=14; EFC, n=6; ENC, n=6; values are means±SE. In the bottom panel, the gastrocnemius muscle mass to body ratio is statistically significant for the nerve fibroblast construct (ENC) compared to native nerve: *p≤0.05; native, n=4; EFC, n=3; ENC, n=3; values are means±SE. The horizontal line indicates the muscle mass decreases by 60% following 28 days of complete denervation, as shown in previous studies.
Figure 4:
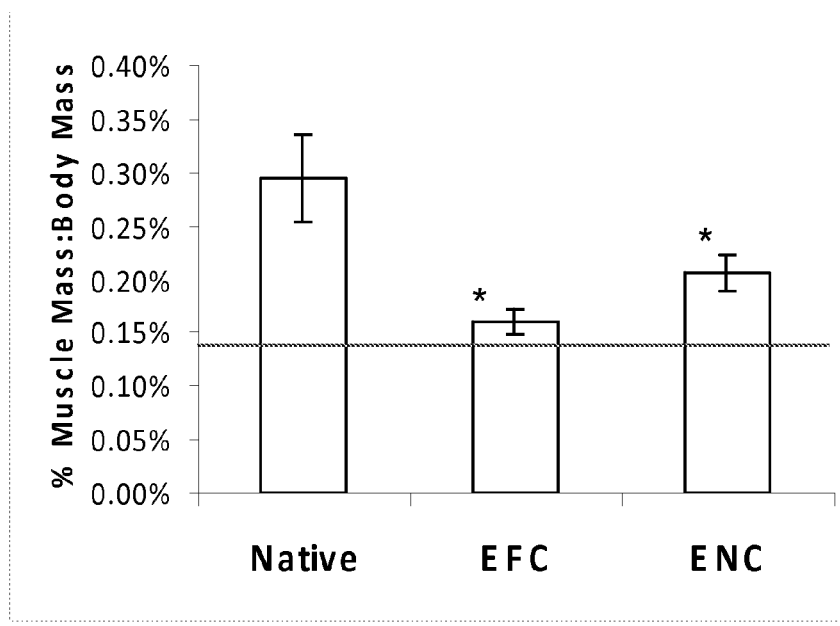

Previous experiments have shown muscle mass to decrease by 60% following 28 days of complete denervation, as indicated by the red line in FIG. 4. In this model, while muscle mass in the control construct and the nerve fibroblast construct decreased compared to non-denervated muscle, these constructs were able to maintain percent mass ratios above that observed with complete denervation (see FIG. 4).

From these results of the non-critical gap nerve gap model using either the nerve fibroblast construct or the control construct, the engineered nerve fibroblast construct showed no observable immune rejection or scar formation. In addition, regenerating nerve traversed the 1 cm gap through both constructs, more so in the nerve fibroblast construct. Nerve conduction velocity was somewhat restored. And finally, the limited force production measures indicated the regenerating nerve reached and innervated the target tissue.

Critical Nerve Gap Model

To further assess the capabilities of our engineered nerve fibroblast construct, the nerve gap was increased to 2 cm in the peroneal nerve. Due to the anatomical limitations of producing a 2 cm gap in the tibial nerve, the gap was generated in the peroneal nerve, which allowed for larger nerve transections and the ability to assess nerve regeneration to two target tissues: the tibialis anterior, used for nerve conduction velocity, and the extensor digitorum longus (EDL), used for contractile properties. Autograft repairs of the transected section of the peroneal nerve were used as negative controls.

From this autograft explant, integration of the autograft into the proximal and distal nerve stumps was observed. Proximal sections were taken 2 mm past the proximal transection. Compared to the native tibial nerve, regeneration of native peroneal nerve, confirmed by the presence of NCAM, was observed through the autograft. Regenerating nerve was also observed filling most of the autograft at 1 cm. The recovery time did not allow for complete nerve regeneration due to a variable rate of regeneration.

The nerve fibroblast construct also had exceptional integration into the native peroneal nerve stumps. NCAM staining confirmed nerve regeneration at the proximal end, albeit approximately 80%. Regenerating nerve at 1 cm was observed filling 20% of the nerve fibroblast construct, located mainly in the periphery.

Figure 5:
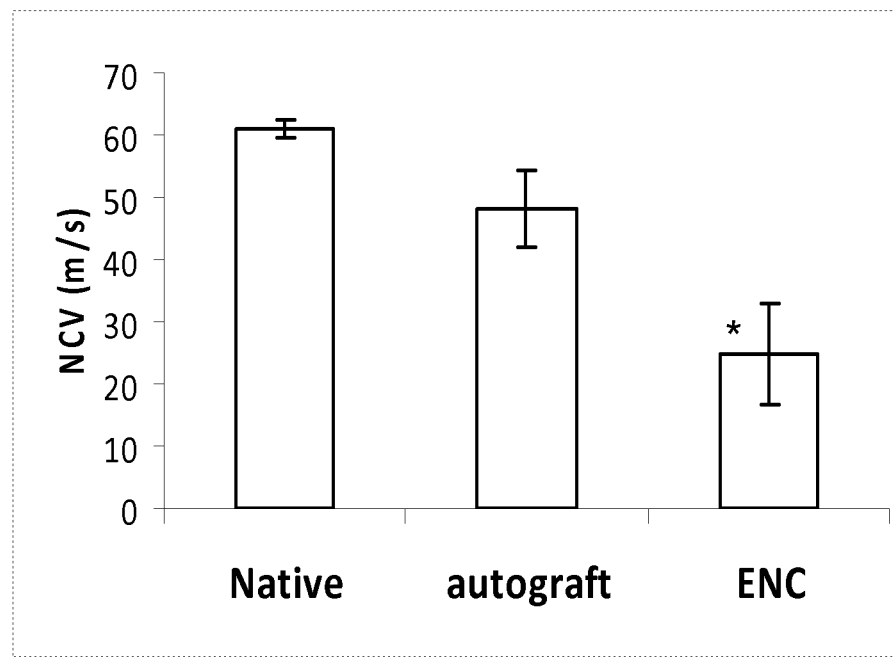
FIG. 5 provides the nerve conduction velocity and the EDL muscle mass to body mass ratio in the critical nerve gap model. In the left panel, the nerve conduction velocity for the native nerve and the autograph are statistically significant from nerve fibroblast construct: *p≤0.05; native, n=14; autograft, n=6; ENC, n=6; values are means±SE. In the right panel, the EDL muscle mass to body ratio is statistically significant for the nerve fibroblast construct (ENC) and the autograph compared to native nerve: *p≤0.05; native, n=3; ENC, n=2; autograft, n=1; values are means±SE. The horizontal line indicates that the EDL muscle mass to body mass ratio shows some maintenance of muscle mass compared to complete denervation.
Figure 5:
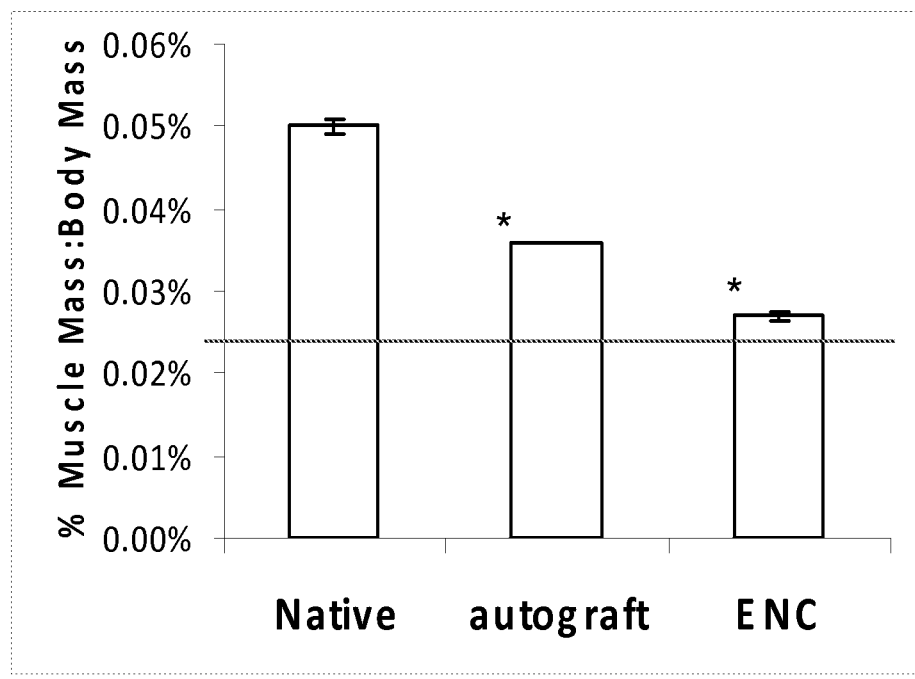

While current literature indicates nerve regeneration rate at approximately 3 mm per day in the rat model, this timeframe was determined to be insufficient for the constructs in the critical gap model. Thus, the functional evaluation of the animals that were studied, indicated incomplete restoration of conduction velocity, shown in the left panel of FIG. 5. At 22 days, the nerve conduction velocity observed in the autograft controls and the nerve fibroblast constructs were 80% and 40% of native nerve, respectively.

Even though EDL muscle mass to body mass ratio showed some maintenance of muscle mass compared to complete denervation, indicated by the red line, re-innervation to the target tissue was shown to be incomplete as we were incapable of eliciting nerve stimulated force production in any of the target muscles.

Example 6

Nerve Fibroblast Construct in Periphereal Nerve Injury Repair

The nerve fibroblast construct was analyzed as an alternative to the autograph in peripheral nerve injury repair. Utilizing Fisher F344 female rats as the animal model for nerve injury, a 10 mm segment of the tibial nerve were transsected and removed. The gap was repaired by suturing in either a Nerve Fibroblast Construct as described in Example 3 (also referred to "engineered nerve construct or ENC), an Engineered Fibroblast Conduit (EFC) which only comprised isolated fibroblasts, an autograft or an non-operative control. This surgical procedure resulted in complete dennervation of both the lateral and medial gastrocnemius muscles. After 12 weeks of recovery, the restoration of function to these muscles was used to assess regeneration of the nerve.

Immunohistochemical analysis of the nerve was performed using SM312, an antibody cocktail marking phosphorylated neurofilament processes and the extracellular matrix marker WGA. Both the neural conduit and fibroblast only conduit allowed for nerve regeneration as indicated by the presence of axons seen 5 mm (mid-way) into the conduit. Axonal fiber counts appeared to be similar in all three surgical innervations compared to the non-surgical control. Structural organization and axon fiber sizes in the ENC appear similar to the non-surgical control, forming perhaps a similar collagen compartmentalization around the regenerating nerve fibers.

Hematoxylin and eosin (H&E) stained frozen sections of medial gastrocnemius muscle was used to analyze muscle fiber atrophy and cross sectional area. Central verses peripheral nuclei was also analyzed as which as an indication of muscle fiber innervation. Measures of cross sectional area indicated that following 12 weeks of recovery autografts had only 4% atrophy compared to 27% and 44% atrophy in ENC and EFC repair. All 3 repair groups faired better than the non-recovery which experienced an 80% atrophy.

Nerve conduction velocity (NVC) was measured as described in Example 4. The autograft repair group restored nerve conduction velocity to 96% of native NCV. The neural conduit and fibroblast conduit repair groups restored nerve conduction velocity to 87% of non-surgical control. This suggests that all three surgery treatments allowed for a re-establishment of the nerve-muscle signal pathway.

Compared to a denervated model, which experienced 12 weeks of atrophy, all three repair models experienced some extent of muscle recovery. This suggests that regenerating nerve fibers reached the target tissue. The recovery of muscle mass in the autograft, compared to the ENC and EFC muscles, suggests that the nerve fibers either regenerated at a faster rate or more of the nerve fibers were able to re-establish functional neuromuscular junctions in the autograft model compared to either the ENC or EFC.

The maximum isometric force data produced by the medial gastrocnemius muscle indicated an increase in nerve recruitment of target muscle fibers in the autograft group (60% of native) than in ENC or EFC (both recovered to only 20% of the native control). The specific force of the autograft was fully recovered, suggesting that all muscle fibers were being recruited for force production but had not yet recovered maximal force production which may be improved by a longer recovery time. The specific forces of the ENC and EFC were 40% of the native and the autograft group data. This suggests that the portion of muscle fibers which were reinnervated and recruited for force production may had not yet recovered maximal force production and there may be a portion of muscle that is not innervated.

This study demonstrates that the Nerve Fibroblast Construct partially restored function in 10 mm peripheral nerve repair. These data suggests that the ENC allows for nerve regeneration following peripheral nerve repair and with some optimization may be a viable alternative for nerve repair to an autograft

Example 7

Utilization of Adipose-Derived Stem Cells (ASC) to Fabricate Scaffoldless Nerve Fibroblast Constructs Isolation of ASCs The ASC isolation protocol is derived from the isolation techniques described in Yamamoto (2007) and Gronthos (2001), both incorporated herein by reference. Briefly, excised adipose tissues were stored in a transfer medium (TM) [Dulbecco's phosphate buffered saline (DPBS Invitrogen), 2% antibiotic/antimycotic (ABAM, Invitrogen)] and placed in ice until processed. The adipose tissue was removed from the TM and rinsed in 70% EtOH and DPBS. After rinsing, the adipose tissue was finely minced using forceps and a razor blade. The minced tissue was then placed in Dissociation Medium (DM) [DPBS, 1% Trypsin (0.25%)/EDTA (Invitrogen), and 0.1% Collagenase 1 (Invitrogen): filtered through a 0.22 pm Steriflip (Millipore)] and set in a 37° shaking water bath for 20 minutes. Once dissociation was complete, the buoyant top layer, containing undissociated adipose tissue, was removed and the remnant was filtered through a 70 pm mesh filter. The sample was then centrifuged at 500×G for 10 minutes, the supernatant was aspirated, and the pellet was resuspended in "growth medium 2" (GM2) (Dulbecco's modified eagle medium (DMEM Invitrogen), 20% fetal bovine serum (FBS Invitrogen), 1% ABAM supplemented with 6 ng/ml FGF-2 (Peprotech). The cell suspension was preplated for 4 hours at which point the medium was changed, removing and discarding non-adherent cells. This ASC passage 0 culture was re-fed 4 days later with FGF-2 supplemented GM2. The ASC culture was then fed FGF-2 supplemented GM2 every other day until the monolayer became >90% confluent at which point the cells were passaged. The purity of the cell population was promoted by repeated passaging and by "forcefully" rinsing the newly seeded ASCs within the first few hours after passaging to allow for the more adherent cells to attach as recommended (Locke 2011). ASCs were passaged 3 times before being used in any differentiation protocols.

Undifferentiated ASCs were continually passaged in GM2 supplemented with 6 ng/ml FGF-2 until they were induced into a fibroblast or nerve lineage as described below. To test the rate of proliferation when FGF-2 was supplemented in the GM2, 50,000 undifferentiated ASCs were seeded in a 48 well plate and given GM2 with and without FGF-2. To allow the ASCs to reach their first logarithmic growth phase, ASCs were fed for four days before being counted (Zhu 2008). The doubling time (Td) was assessed in order to determine the rate of proliferation. Doubling time was calculated using time of seeding ($t_1$), time of assessment ($t_2$), seeding cell density ($q_1$), and living cells at $t_2$ ($q_2$) in the following equation:

$$Td=(t_2-t_1)*(\log 2/\log(q_2/q_1))$$

Cell viability was confirmed utilizing Trypan blue stain.

Figure 6:
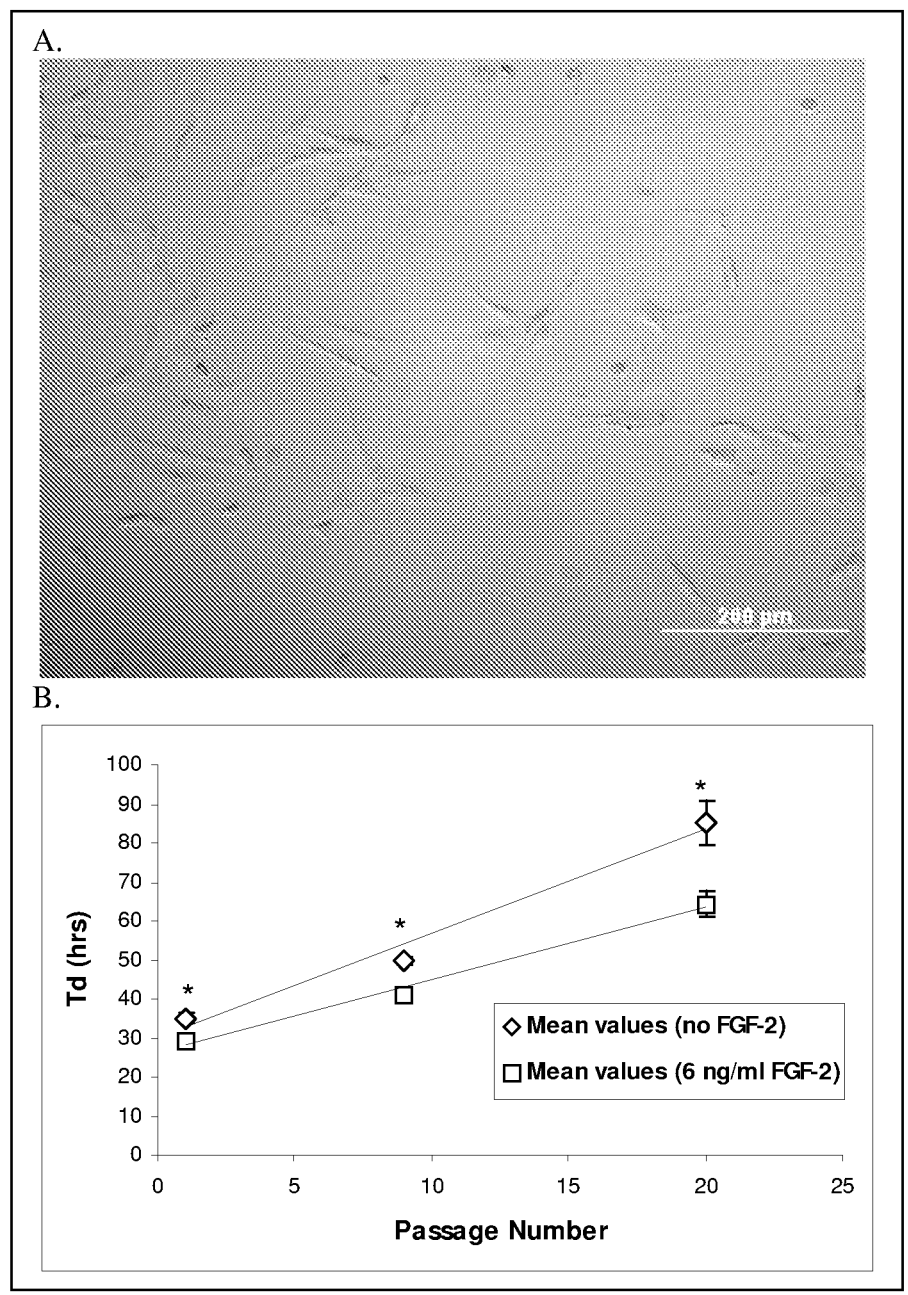
FIG. 6 depicts the spindle shaped morphology of undifferentiated ASCs at passage 3. Phase contrast at 40× magnification (A). Doubling time (Td) of ASCs at different passage number and with or without the addition of FGF-2 added to the growth medium (B). The addition of FGF-2 to undifferentiated ASCs significantly decreased their Td. The statistical significance of the addition of FGF-2 to undifferentiated ASCs increased in later passages as compared to earlier passages. *p<0.05, compared to treatments with 6 ng/ml FGF-2.

The ASCs were observed to have the reported spindle-shaped morphology, beginning at passage 0 and up through passage 12 (FIG. 6). Undifferentiated ASC populations from passage 0 exhibited negative staining for adipocyte dye Oil Red O (Sigma Aldrich).

Optimizing Proliferation with FGF-2

The current protocol utilized growth medium supplemented with FGF-2 to increase the rate of proliferation of the undifferentiated ASCs. Rate of proliferation or doubling time (Td) was calculated for proliferation experiments in growth media 2 (GM2) with and without FGF-2. The total cell count after 3 days in vitro was taken and compared to the initial seeding density utilizing the doubling time equation (Zhu 2008). The Td values were entered on a scatter plot to assess the changes in proliferation rates of ASC populations at passages 1, 9, and 20 both with and without the addition of 6 ng/ml FGF-2 (FIG. 6). Proliferation was slower for cells at later passages. ASCs which were given FGF-2 decreased Td by 20% in passage 1 and 9 and by 25% in passage 20.

Fibroblast Differentiation

The cell source for fibroblast differentiation was a portion of undifferentiated ASC plates once they had been passaged 3 times. The ASCs were seeded in 60 mm tissue culture treated plates at approximately 400,000 cells. ASCs were seeded in GM2 supplemented with 6 ng/ml FGF-2 and 130 ng/ml Ascorbic Acid-2-phosphate with 50 ng/ml Proline (AA2P, Sigma Aldrich). Plates were fed supplemented GM2 every other day for at least 5 days until the monolayer reached >90% confluence. At this confluence level, several plates of cells were fixed in 4% paraformaldehyde (PFA) and stained for Collagen 1 (Col1) to validate the induction and differentiation into the fibroblast lineage. The remaining plates were used to fabricate conduits.

The optimal concentration of FGF-2 and AA2P to induce ASCs to fibroblasts was evaluated by growing ASCs in GM2 with different concentrations of both growth factors. The initial concentrations of 6 ng/ml FGF-2 and 130 ng/ml AA2P was established previously (Ma 2009). Concentrations of 6, 3, and 0 ng/ml FGF-2 were tested in combination with 130, 65, and 0 ng/ml AA2P. Fifty thousand undifferentiated ASCs were seeded in a 48 well plate and fed GM2 with FGF-2 and AA2P for 3 days at which time plates were fixed with 4% PFA and stained for Col1. Optimal concentrations of FGF-2 and AA2P were determined by measuring the percent of Col1 positive cells produced.

During the induction phase of fibroblast differentiation (between 5-7 days) and before reaching confluence over 90% of the differentiated ASCs expressed the fibroblast marker Col1. The effects of varying concentrations of FGF-2 and AA2P with proline on fibroblast induction and differentiation was quantified by calculating the percentage of cells staining positively for Col1. Treatments with no growth factors or only FGF-2 (6 ng) resulted in a minimal percentage of Col1 positive cells (5-10%). The addition of 6 ng of FGF-2 increased the Col1 positive cell population to 73%. The treatment with only AA2P (130 ng) with proline (50 ng) and no FGF-2 increased fibroblast differentiation to 50% Col1 positive cells. Thus, the optimal concentrations of growth factors for differentiation were 130 ng of AA2P with 50 ng proline and 6 ng FGF-2 which resulted in 90% Col1 positive cells. Once confluent and fed DM, the fibroblast monolayer was observed undergoing delamination due to the switch to low serum media. The monolayer was manually formed into a cylinder and held in place by constraint pins. The conduit remodeled into a 16-24 long fibroblast conduit, referred to an aEFC.

Adipose-Derived Stem Cell Engineered Fibroblast Conduits (aEFC) Fabrication:

Once the ASCs were induced to a fibroblast lineage and reached >90% confluence, the medium was switched to differentiation medium (DM) (DMEM, 7% horse serum (Invitrogen), 1% ABAM) supplemented with 6 ng/ml FGF-2, 130 ng/ml AA2P with 50 ng/ml Proline, and 12 ng/ml transforming growth factor TGF-β1 (Peprotech). The supplemented DM2 was changed every other day for 7-10 days until the edges of the monolayer were observed to start to delaminate at which point the monolayer was manually formed into a cylinder, transferred to a sylgard-coated dish (WPI), and pinned using minutien constraint pins forming a 16-24 mm long cylindrical aEFC. The aEFCs were pinned and fed GM2 until conduits were observed to become taut at which point they were frozen in Tissue Tek (Fisher) and preserved for histology.

Neurogenesis

The neurosphere induction protocol was derived from methods used by Radtke (2009) and Bunnell (2008), incorporated herein by reference. Briefly, ASCs were obtained from primary ASC culture at passage 3 or later, and ASCs were seeded on Pyrex plates (Falcon) at 1,000 cells per ml of neural basal medium 2 (NBM2) supplemented with 1% N2 (Invitrogen), 1% ABAM, 1% B27 (Invitrogen), 10 ng/ml epidermal growth factor (EGF Invitrogen), and 10 ng/ml FGF-2. N2 and B27 are commonly used, serum-free, growth factor cocktails which are used to promote and sustain neural growth.

Neurosphere induction cultures were observed for 3 days, replenishing EGF and FGF-2 each day. The concentrations of EGF and FGF-2 needed to induce ASCs to neurospheres were evaluated by observing the amount and size of the neurospheres produced when varying concentrations were added to the induction medium. Fifty thousand undifferentiated ASCs were seeded on sylgard coated 12 well plates in NBM2 supplemented with N2, ABAM, B27, and various concentrations of EGF and FGF-2. On day 3, phase contrast images were taken to assess the count and size of neurospheres. These neurospheres were then transferred to adherent tissue culture treated dishes to induce glial-like cell differentiation.

To differentiate neurospheres to glial-like cells, free-floating neurospheres were collected and centrifuged at 800×G for 10 minutes. Pelleted neurospheres were resuspended in NBM2 supplemented with B27. These cultures were fed B27 supplemented NBM2 every other day for 7-10 days either on tissue culture treated dishes (then fixed for histology) or on top of an ASC-induced fibroblast monolayer ASC engineered neural conduit (aENC) formation.

Neurosphere differentiation into glial-like cells was accomplished using differentiation medium 2 [(DM2), NBM2 supplemented with 1% B27, 1% ABAM, and 1% N2]. To test the effects of serum and growth factors on neurospheres, experimental treatments were fed DM2 with 10% FBS, DM2 with 10 ng/ml EGF and 10 ng/ml FGF-2, or serum-based growth medium, GM2. The neurospheres were fed DM2 for 3 days at which point the neurospheres were assessed for ability to attach and extend neural processes. Successful differentiation was determined by the size and number of neurospheres produced as well as the presence of neural processes and neural marker S100.

Figure 7:
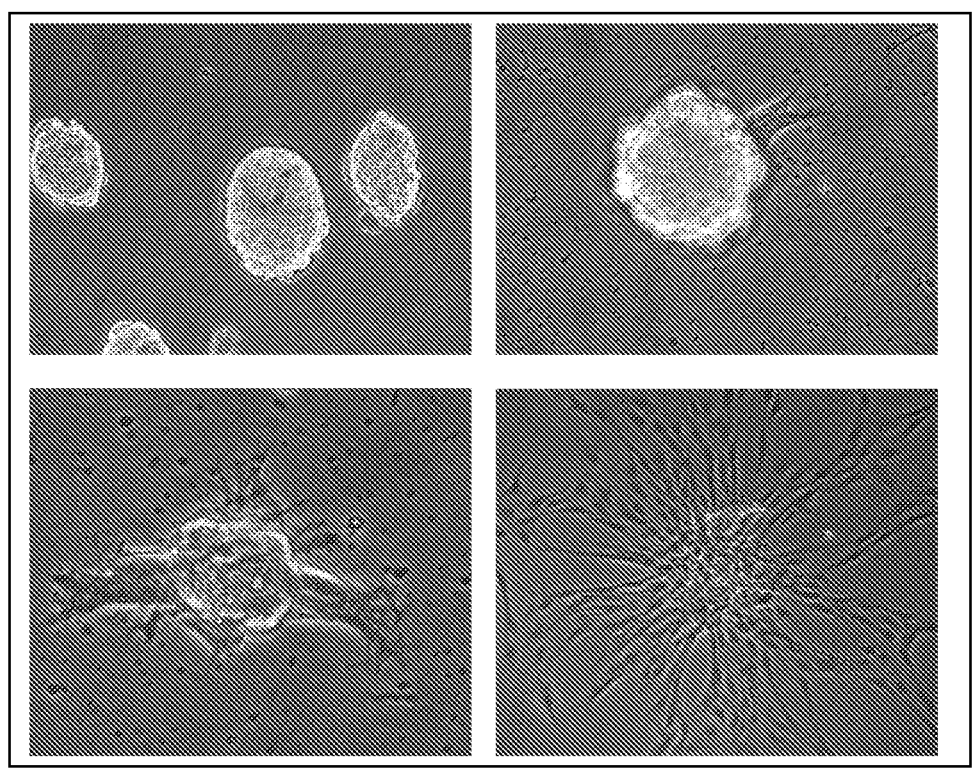
FIG. 7 depicts the neurospheres observed as free-floating aggregates of cells (A) which began to attach 1 day after being transferred to an adherent surface (B). On day 3 more cells were observed attaching to the plate (C) By day 7, nearly all cells from the neurosphere attached to the plate and extended neural processes (D). Phase contrast at 40× magnification.

Neurosphere aggregates were observed to form on non-adherent Pyrex® plates in EGF and FGF-2 supplemented serum-free NBM2 (FIG. 7A). When transplanted to an adherent surface and fed NBM2 without supplemented growth factors, the neurospheres attached and formed neural processes (FIG. 7B-D). These glial-like cells were shown to be distinct from the ASC-derived fibroblasts in co-culture, staining negative for Col1 and positive for S100 (FIG. 9B).

Figure 8:
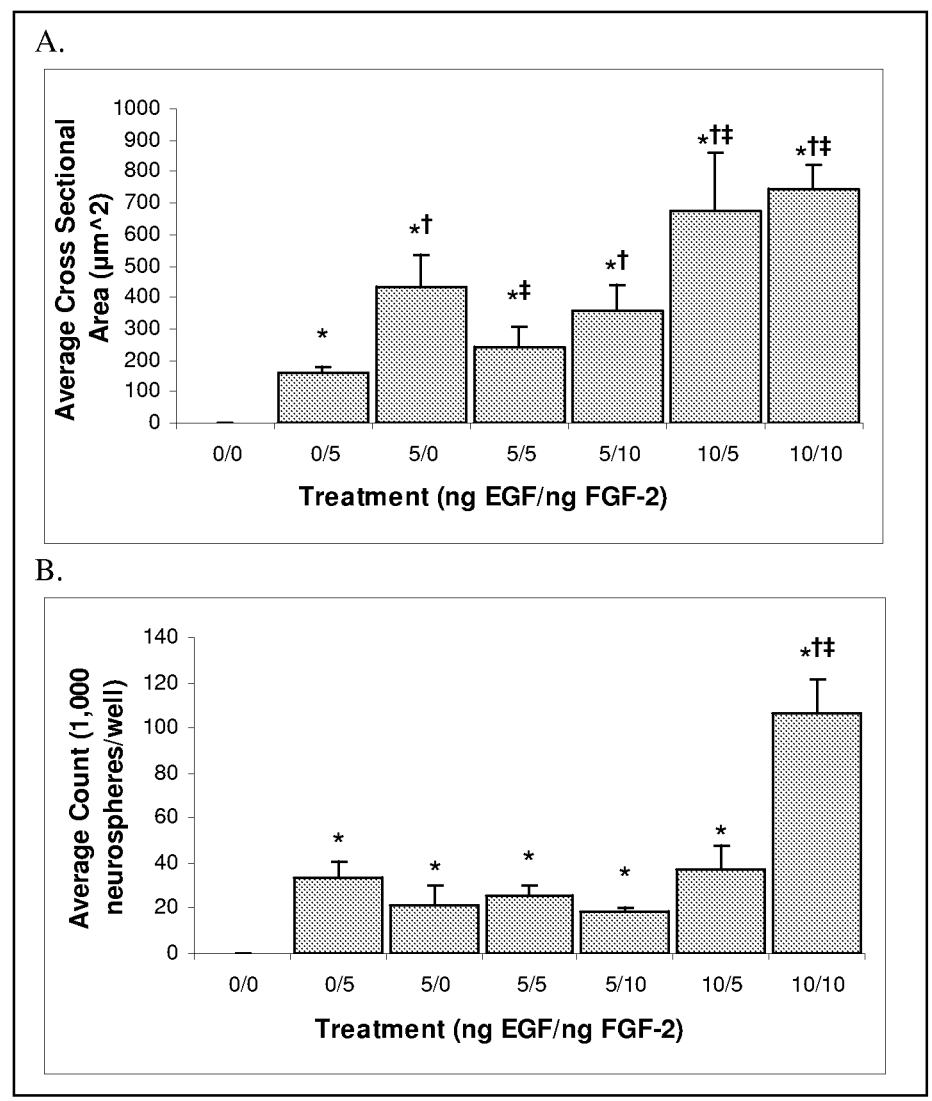
FIG. 8 depicts neurosphere induction at different concentrations of EGF and FGF-2. Between 30 and 80 neurospheres were measured from each treatment to find the average cross sectional area, CSA (A). Without EGF or FGF-2 no neurospheres accumulated. Treatments with 5 ng of EGF produced neurospheres of a statistically similar CSA with or without the addition of FGF-2. Additionally neurospheres from treatments with 10 ng of EGF had similar CSA whether or not FGF-2 was added. The total number of neurospheres in each well for each treatment was also counted (B). The treatment with 10 ng of both EGF and FGF-2 resulted in significantly more neurospheres per well than any other treatment. All other treatments yielded no significant difference from each other. *p<0.05, compared to negative control; † p<0.05, compared to treatment with 0 ng/ml EGF and 5 ng/ml FGF-2; ‡<0.05, compared to treatment with 5 ng/ml EGF and 0 ng/ml FGF-2.

Neurosphere induction was tested using 9 combinations of 0, 5, and 10 ng/ml of both EGF and FGF-2. The number and cross sectional area of neurospheres per well were calculated (FIG. 8). When both EGF and FGF-2 were absent from the induction medium, no neurospheres were observed. It was observed that the concentration of 10 ng/ml EGF in combination with 10 ng/ml FGF-2 was optimal for neurosphere induction (FIG. 8). With treatments using less than 10 ng/ml EGF and 10 ng/ml of FGF-2, fewer and smaller neurospheres were observed. Treatments with only EGF supplementation gave rise to larger neurospheres (432 pm$^2$) than treatments with only FGF-2 (158 pm$^2$). The treatments with 10 ng of EGF in combination with either 10 ng/ml or 5 ng/ml of FGF-2 gave rise to the largest neurospheres (675-750 pm$^2$). However the treatment of with 10 ng/ml of EGF and 10 ng/ml of FGF-2 produced significantly more neurospheres ($1.06 \times 10^5$) than treatments of 10 ng/ml of EGF with only 5 ng/ml of FGF-2 ($3.75 \times 10^4$).

Figure 9:
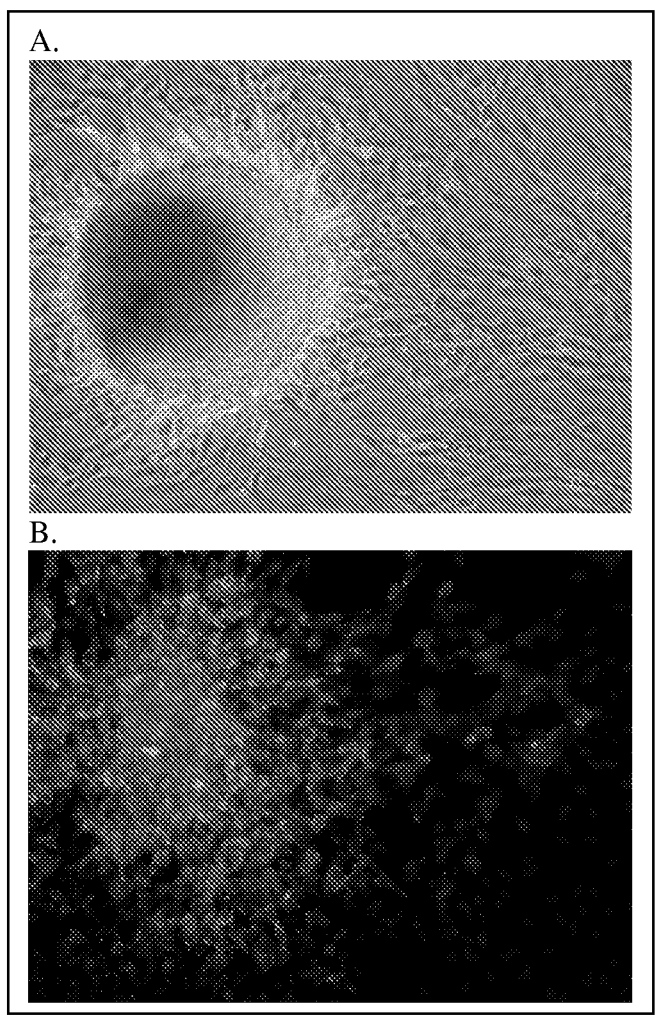
FIG. 9 depicts co-cultures with ASC-derived fibroblasts monolayer (black arrow). Neurospheres (white arrow) were observed attaching and expanding on the fibroblast monolayer (A). Phase contrast at 40× magnification. The glial-like cells (small arrows) coming from the neurosphere (large arrow) migrated onto the fibroblast monolayer as indicated by positive staining for Schwann cell marker S100 (A). S100 DAPI at 40× magnification.

The glial-like cell differentiation of neurospheres was confirmed by the presence of S100 positive cells (FIG. 9B). When neurospheres were seeded in serum-based medium (GM2 or NBM2 with 20% FBS) one of two observations were made. Either the cells did not attach to the dish or the resulting cells returned to a spindle-shaped undifferentiated morphology with no processes. Neurospheres seeded in NBM with EGF and FGF-2 resulted in similar glial-like cells as compared to the neurospheres seeded in only NBM2 (FIG. 9).

Adipose-Derived Stem Cell Engineered Neural Conduit (aENC) Fabrication

After ASC-induced fibroblast monolayers reached >80% confluence on GM2, neurospheres were seeded on top of them. The co-culture was fed NBM2 supplemented with B27, so as to allow for expansion of the neural cells while simultaneously arresting the growth of the fibroblasts. After 7-10 days, a neural network was established and the cells were fed FGF-2 and AA2P supplemented GM2 to recover the fibroblasts. After 3 days the medium was switched to TGF-β1 and AA2P supplemented DM2, as in the case of the aEFCs. The supplemented DM2 was changed every other day for 7-10 days until the edges of the monolayer were observed to start to deliminate at which point the monolayer was manually formed into a cylinder, \transferred to a sylgard-coated dish, and pinned in place. Once pinned, the (aENC) were fed GM2 until taut, at which point they were frozen in Tissue Tek and preserved for histology.

Histology

For immunohistochemical analysis, cell populations were rinsed in DPBS (3 times for 10 minutes each) then fixed with 4% paraformaldehyde for 45 minutes. Cells were permeabilized with 0.2% Triton X-100 (Sigma) for 10 minutes, followed by a 30 minute blocking step in 5% Donkey Serum (Sigma). Cells were incubated overnight at 4° C. with primary antibodies (Col1, S100) at a dilution of 1:100. Cells were then incubated with AlexaFluor 488 or 555-conjugated secondary antibodies (Abcam) for 1 hour at room temperature. Cells were incubated with 2% DAPI for 5 minutes. The antibody positive cells were then observed by confocal microscopy using a Leica Inverted microscope.

Conduit Formation

Figure 10:
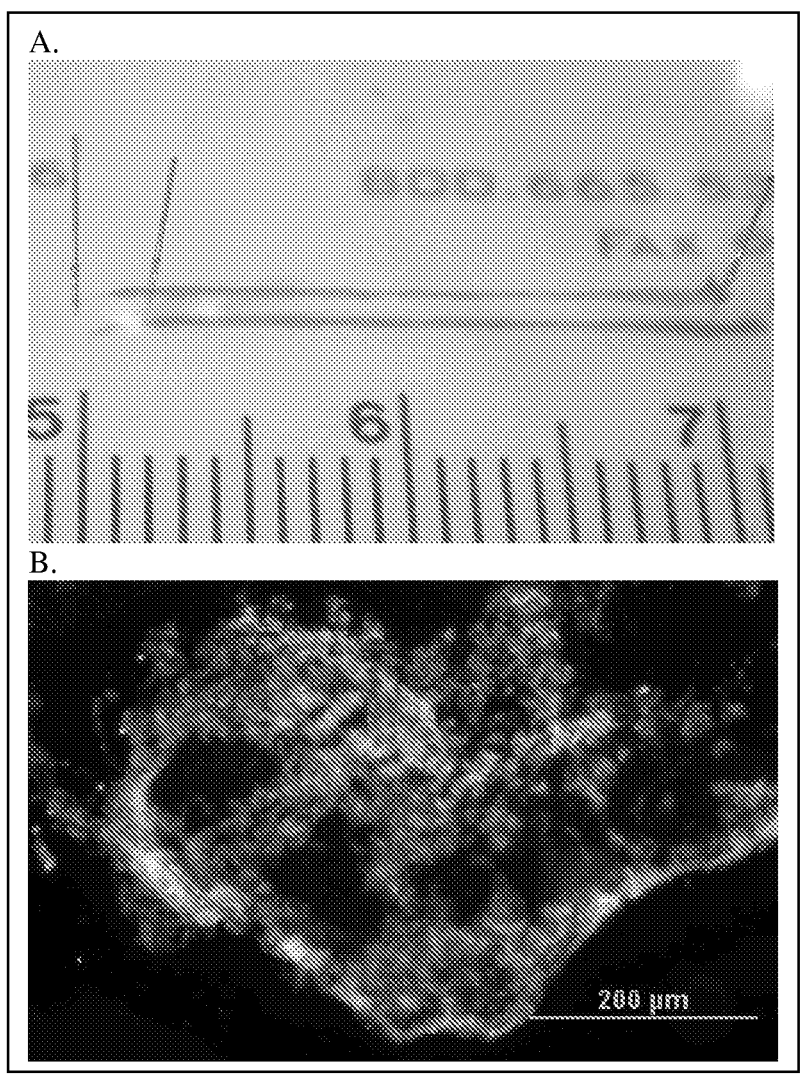
FIG. 10 depicts the three-dimensional formation of engineered neural conduit fabricated from ASC-induced fibroblasts and ASC-induced glial-like cells (aENC) at 20 mm length in vitro (A). The numbers depicted on the ruler are in centimeters. The smallest graduated line is in millimeters. The presence of both fibroblast and glial-like cell types in the aENC cross section were confirmed using collagen marker Col1 and S100 (B). Fibroblasts were observed surrounding an inner neural network.

Like the aEFC previously described, the co-culture of glial-like cells and ASC-derived fibroblasts delaminated and formed a 3-dimensional engineered neural conduit, aENC, (FIG. 10A). The length of the aENCs was pre-customized between 20 and 45 mm depending on the size of the dish in which the monolayer was made (FIG. 10A). The thickness of the aENCs was measured at a range of 0.3 to 1.0 mm. Histology of the aENC was performed 7 days after formation and revealed fibroblasts forming an epineurial-like sheath surrounding an inner neural network (FIG. 10B). The fibroblasts of the aENC stained positive for Col1 and were observed encasing the conduit as well as throughout the center. The S100 positive glial-like cells were observed within the conduit.

Statistics

Statistical comparisons were performed using values of means±standard error (SE) to determine statistical significance. When two groups were compared the student's T-test was performed. Comparisons of 3 groups or more were performed by one-way ANOVA tests. Statistical significance was recognized at $p<0.05$. Differences yielding a $p<0.001$ were also noted in the figures.

REFERENCES

1. Balgude A P, Yu X, Szymanski A and Bellamkonda R V. 2001. Agarose gel stiffness determines rate of DRG neurite extension in 3D cultures. Biomaterials. 22:1077-84.
2. Bellamkonda R, Ranieri J P, Bouche N, and Aebischer P. A Hydrogel based three-dimensional matrix for neural cells. J Biomedical Materials Research. 29(1995): 663-671.
3. Bryan D J, Tang J B, Doherty S A, Hile D D, Trantolo D J, Wise D L, and Summerhayes I C. Enhanced peripheral nerve regeneration through a poled bioresorbably poly (lactic-co-glycolic acid) guidance channel. J Neural Eng. 2004. 1.2:91-98.
4. Bunge, M B, Bunge R P, Kleitman N, et al. Role of peripheral nerve extracellular matrix in Schwann cell function and in neurite regeneration. Dev Neurosci. 1988; 11:348-360.
5. Calve, S., et al., Engineering of functional tendon. Tissue Eng, 2004. 10(5-6): p. 755-61.
6. Chiu D T. 1995. Special article: the development of autologous venous nerve conduit as a clinical entity. In P&S Medical Review, 3(1). New York: Columbia-Presbyterian Med. Cent.
7. Ceballos D, Navarro X, Dubey N, Wendelschafer-Crabb G, Kennedy W R and Tranquillo R T. Magnetically aligned collagen gel filling a collagen nerve guide improves peripheral nerve regeneration. Exp Neurol. 1999. 258.2:290-300.
8. Galla T J, Vedecnik S V, Halbgewachs J, Steinmann S, Friedrich C, and Stark G B. Fibrin/Schwann cell matrix in poly-epsilon-caprolactone conduits enhances guided nerve regeneration. Int J Artif Organs. 2004. 27.2:127-136.
9. Huang Y C and Huang Y Y. Biomaterials and Strategies for Nerve Regeneration. Articial 2006. 30.7:514-522.
10. Hudson, T. W., Gregory R. D. Evans and Christine E. Schmidt. Engineering Strategies for Peripheral Nerve Repair. Orthopedic Clinics of North America. 31.3(2000): 485-498.
11. Lundborg G. 1988. Nerve Injury and Repair. New York: Longman Group UK.
12. Luo Y and Schoichet M S 2004 A Photoliable hydrogel for guided three-dimensional cell growth and migration. Nat Mater. 3: 249-253.
13. Millesi H. Indications and techniques of nerve grafting. In: Gelvertman R H, editor. Operative nerve repair and reconstruction. Philadelphia: Lippincott J B, 1991. 525-544.
14. Millesi, H. Briding defects: Autologous nerve grafts. Acta Neurochir Suppl. (2007) 100: 37-38.
15. Piotrowicz A and Shoichet M S. Nerve Guidance channels as drug delivery vehicles. Biomaterials. 2006. 27.9: 2018-2027.
16. Rutkowski, G. E., Cheryl A Miller, Srdija Jeftinija, and Surya K Mallapragada. Synergistic Effects of Micropatterened Biodegradable Conduits and Schwann Cells on Sciatic Nerve Regeneration. Journal of Neural Engineering. 1(2004): 151-157.
17. Schmidt, C. E. and Jennie Baier Leach. Neural Tissue Engineering: Strategies for Repair and Regeneration. Annu. Rev. Biomed. Eng. 5(2003): 293-347.
18. Seidlits, S. K., J. Y. Lee, and C. E. Schmidt, Nanostructured scaffolds for neural applications. Nanomed, 2008. 3(2): p. 183-99.
19. Spilker, M. H., K Asano, IV Yannas and M Spector. Contraction of collagen-glycosaminoglycan matrices by peripheral nerve cells in vitro. Biomaterials. 22(2001): 1085-1093.
20. Yu X. George P Dillon, Ravi V. Bellamkonda. A Laminin and nerve growth factor-laden three-dimensional scaffold for enhanced neurite extension. Tissue Engineering. 5.4 (1999):291-305.
21. Baltich, J., Hatch-Vallier, L., Adams, A. M., Arruda, E. M., & Larkin, L. M. (2010). Development of a scaffoldless three-dimensional engineered nerve using a nerve-fibroblast co-culture. In Vitro Cellular & Developmental Biology. Animal, 46(5), 438-444.
22. Deumens, R., Bozkurt, A., Meek, M. F., Marcus, M. A., Joosten, E. A., Weis, J., et al. (2010). Repairing injured peripheral nerves: Bridging the gap. Progress in Neurobiology, 92(3), 245-276.
23. Gronthos, S., Franklin, D. M., Leddy, H. A., Robey, P. G., Storms, R. W., & Gimble, J. M. (2001). Surface protein characterization of human adipose tissue-derived stromal cells. Journal of Cellular Physiology, 189(1), 54-63.

24. Locke, M., Feisst, V., & Dunbar, P. R. (2011). Concise review: Human adipose-derived stem cells (ASC): Separating promise from clinical need. Stem Cells (Dayton, Ohio)

25. Ma, J., Goble, K., Smietana, M., Kostrominova, T., Larkin, L., & Arruda, E. M. (2009). Morphological and functional characteristics of three-dimensional engineered bone-ligament-bone constructs following implantation. Journal of Biomechanical Engineering, 131(10), 101017.

26. Radtke, C., Schmitz, B., Spies, M., Kocsis, J. D., & Vogt, P. M. (2009). Peripheral glial cell differentiation from neurospheres derived from adipose mesenchymal stem cells. International Journal of Developmental Neuroscience: The Official Journal of the International Society for Developmental Neuroscience, 27(8), 817-823.

27. Ray, W. Z., & Mackinnon, S. E. (2010). Management of nerve gaps: Autografts, allografts, nerve transfers, and end-to-side neurorrhaphy. Experimental Neurology, 223(1), 77-85.

28. Yamamoto, N., Akamatsu, H., Hasegawa, S., Yamada, T., Nakata, S., Ohkuma, M., et al. (2007). Isolation of multipotent stem cells from mouse adipose tissue. Journal of Dermatological Science, 48(1), 43-52.

29. Zhu, Y., Liu, T., Song, K., Fan, X., Ma, X., & Cui, Z. (2008). Adipose-derived stem cell: A better stem cell than BMSC. Cell Biochemistry and Function, 26(6), 664-675.

30. Hudson, T. W., Evans, G. R., & Schmidt, C. E. (2000). Engineering strategies for peripheral nerve repair. The Orthopedic Clinics of North America, 31(3), 485-498.

What is claimed is:

1. A self-organizing, scaffold-free, three-dimensional nerve-fibroblast construct comprising an inner core of nerve cells surrounded by an external sheath of fibroblasts for use in repairing a nerve transection or replacing damaged tissue, wherein neural markers are absent from the fibroblast sheath.

2. The construct of claim 1, wherein the fibroblasts or nerve cells are derived from adipose-derived stem cells.

3. The system of claim 1, wherein the fibroblasts and nerve cells are derived from adipose-derived stem cells.

4. A method of repairing a nerve transection in a subject comprising inserting the three-dimensional nerve fibroblast construct of claim 1 in a subject in need to repair the nerve transection.

5. A method of replacing damaged nerve tissue in a subject comprising inserting the three-dimensional nerve fibroblast construct of claim 1 in a subject in need to replace the damaged nerve tissue.

* * * * *

UNITED STATES PATENT AND TRADEMARK OFFICE
CERTIFICATE OF CORRECTION

| | | |
|---|---|---|
| PATENT NO. | : 9,592,255 B2 | Page 1 of 1 |
| APPLICATION NO. | : 13/805486 | |
| DATED | : March 14, 2017 | |
| INVENTOR(S) | : Lisa M. Larkin et al. | |

It is certified that error appears in the above-identified patent and that said Letters Patent is hereby corrected as shown below:

On the Title Page

At item (57), Line 4, "methods or" should be -- methods of --.

In the Claims

At Column 24, Line 15, "system" should be -- construct --.

Signed and Sealed this
Twenty-sixth Day of December, 2017

Joseph Matal
*Performing the Functions and Duties of the
Under Secretary of Commerce for Intellectual Property and
Director of the United States Patent and Trademark Office*